United States Patent
Flanagan et al.

(10) Patent No.: US 6,919,313 B2
(45) Date of Patent: Jul. 19, 2005

(54) PROTEIN WAVING A PDZ AND A RGS DOMAIN

(75) Inventors: John G. Flanagan, Newton, MA (US); Qiang Lu, Brookline, MA (US); Edna E. Sun, Brookline, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 390 days.

(21) Appl. No.: 10/113,794

(22) Filed: Apr. 1, 2002

(65) Prior Publication Data

US 2003/0022202 A1 Jan. 30, 2003

Related U.S. Application Data

(60) Provisional application No. 60/280,260, filed on Mar. 30, 2001.

(51) Int. Cl.$^7$ .......................... A61K 38/17; C07K 14/46
(52) U.S. Cl. ............................. 514/12; 530/350; 514/2; 514/8
(58) Field of Search .............................. 530/350; 514/2, 514/8, 12; 435/69.1

(56) References Cited

U.S. PATENT DOCUMENTS

| | | | |
|---|---|---|---|
| 2002/0034494 A1 | 3/2002 | Vicari et al. | 424/85.1 |
| 2002/0081683 A1 | 6/2002 | Hodge et al. | 435/183 |
| 2002/0119973 A1 | 8/2002 | Luly et al. | 514/230.5 |

OTHER PUBLICATIONS

Druey, et al. "Inhibition of G–Protein–Mediated MAP Kinase Activation by a New Mammalian Gene Product," *Nature*, 1996, vol. 379, pp. 742–746.

Lu, et al. "Ephrin–B Reverse Signaling is Mediated by a Novel PDZ–RGS Protein and Selectively Inhibits G Protein–Coupled Chemoattraction," *Cell*, Apr. 2001, vol. 105, pp. 69–79.

*International Search Report*, dated Sep. 29, 2003, received Oct. 1, 2003.

Reif et al. "RGS Molecule Expression in Murine B Lymphocytes and Ability to Down–Regulate Chemotaxis to Lymphoid Chemokines," The Journal of Immunology, 2000, 4720–4729.

Haeyoung Kong et al. "An Evolutionarily Conserved Transmembrane Protein that is a Novel Downstream Target of Neurotrophin and Ephrin Receptors," The Journal of Neuroscience, Jan, 1, 2001, 21(1):176–185.

Muller et al. "Involvement of Chemokine Receptors in Breast Cancer Metastasis," Nature, Mar. 1, 2001, vol. 410, 50–56.

Jane Y. Wu et al. "The Neuronal Repellent Slit Inhibits Leukocyte Chemotaxis Induced by Chemotactic Factors", Nature, vol. 410, Apr. 19, 2001, 948–952.

*Primary Examiner*—Prema Mertz
(74) *Attorney, Agent, or Firm*—Bromberg & Sunstein LLP

(57) ABSTRACT

Transmembrane B ephrins and their Eph receptors signal hi-directionally. The presently claimed invention describes a cytoplasmic protein, designated PDZ-RGS3, which binds B ephrins through a PDZ domain, and has a regulator of heterotrimeric G protein signaling (RGS) domain. PDZ-RGS3 mediates signaling from the ephrin-B cytoplasmic tail. SDF-1, a chemokine with a G protein coupled receptor, or BDNF, act as chemoattractants for cerebellar granule cells, with SDF-1 action being selectively inhibited by soluble EphB receptor. The claimed invention reveals a pathway that links reverse signaling to cellular guidance, uncovers a novel mode of control for G proteins, and demonstrates a mechanism for selective regulation of responsiveness to neuronal guidance cues. Further, compositions and methods of use are provided for modulating cell migration as a function of chemokines and GPCR interaction, to aid in the treatment of disease states and medical conditions, including cancer and immune responses such as allergy and autoimmune responses. In one embodiment, a method of altering the sensitivity of a cell to a chemokine is provided using a PDZ-RGS3 protein.

3 Claims, 7 Drawing Sheets

PROTEIN WAVING A PDZ AND A RGS DOMAIN

CROSS REFERENCE TO RELATED APPLICATION

This application gains priority from U.S. Provisional Application No. 60/280,260, filed Mar. 30, 2001, which is hereby incorporated by reference in its entirety herein.

GOVERNMENT FUNDING

The invention was made in part with government support under grants HD29417 and NS40043 awarded by the National Institutes of Health. The government has certain rights in the invention.

TECHNICAL FIELD AND BACKGROUND ART

The present invention relates to ephrin reverse signaling in vertebrate cells, particularly cerebellar granular cells and leukocytes, the signaling acting through a novel PDZ-RGS protein, to block a heterotrimeric G protein-pathway. This signaling results in inhibition of the chemoattractant effects of a chemokine, in particular, of SDF-1. Methods and compositions for modulation of the pathway provide potential therapeutic agents for inflammation and autoimmune diseases.

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines ($\alpha$-chemokines), and the C—C chemokines ($\beta$-chemokines), in which the first two conserved cysteines are separated by an intervening residue, or adjacent respectively (Baggiolini, M. and Dahinden, C. A., Immunology Today, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins $1\alpha$ and $1\beta$ (MIP-$1\alpha$ and MIP-$1\beta$), and human monocyte chemotatic proteins 1–3 (MCP-1, MCP-2, MCP-3), which have been characterized as chemoattractants and activators of monocytes or lymphocytes but do not appear to he chemoattractants for neutrophils. Chemokines, such as RANTES and MIP-$1\alpha$, have been implicated in a wide range of human acute and chronic inflammatory diseases including respiratory diseases such as asthma and allergic disorders.

The chemokine receptors are members of a superfamily of G protein-coupled receptors (GPCR) which share structural features that reflect a common mechanism of action of signal transduction (Gerard, C. and Gerard, N. P., Annu Rev. Immunol., 12:775–808 (1994); Gerard, C. and Gerard, N. P., Curr. Opin. Immunol., 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse.

The superfamily of GPCRs has at least 250 members (Strader et al. FASEB J., 9:745–754, 1995; Straderet al. Annu. Rev. Biochem., 63:101–32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). Upon ligand binding, GPCRs regulate intracellular signaling pathways by activating guanine nucleotide-binding proteins (G proteins). GPCRs play important roles in diverse cellular processes including cell proliferation and differentiation, leukocyte migration in response to inflammation, and cellular response to light, odorants, neurotransmitters and hormones (Strader et al., supra.).

Over the last fifteen years it has become apparent that many ligands that signal through cell surface receptors are themselves transmembrane molecules (Pfeffer and Ullrich, 1985; Flanagan et al., 1991; Massague and Pandiella, 1993). One function of this ligand anchorage may be to tightly localize the signal. This idea is particularly well exemplified by the ephrins, since they require membrane anchorage to activate their receptors in a direct cell-cell contact mechanism, and since they have spatially precise patterning roles.

A second potential function for transmembrane ligands is to allow bi-directional signaling. Again, the ephrins have provided a particularly good model system to investigate this idea. Reverse signaling through B ephrins has been demonstrated biochemically by ligand phosphorylation. Evidence of important developmental roles has come from genetic and embryological studies of whole embryos or tissues.

Ligands in the ephrin-B family are cell surface anchored by a transmembrane domain, and signal through their Eph receptors by direct cell-cell contact (Davis et al., 1994; Drescher et al., 1997; Flanagan and Vanderhaeghen, 1998; Frisen et al., 1999; Holder and Klein, 1999; Mellitzer et al., 1999). This contact-mediated mechanism provides the potential for bi-directional signaling, with a forward signal through the tyrosine kinase receptor, and a reverse signal through the ligand. Reverse signaling has been demonstrated biochemically by studies showing B ephrins become phosphorylated upon treatment of cells with soluble EphB-Fc receptor fusion protein (Holland et al., 1996; Bruckner et al., 1997). In the context of whole organisms or tissues, genetic and embryological studies have supported important roles for B ephrin reverse signaling in developmental processes, including axon pathway selection, blood vessel formation, and rhombomere compartmentation (Henkemeyer et al., 1996; Jones et al., 1998; Wang et al., 1998; Adams etal., 1999; Gerety etal., 1999; Mellitzer et al., 1999:Xu et al., 1999). However, little is known of the specific effects of B ephrin reverse signaling on individual cells, or the signal transduction pathways that lead to such effects.

Evidence that B ephrins might interact with cytoplasmic proteins initially came from sequence comparison of ephrin-B1 and -B2, which show a striking 100% amino acid identity in the last 33 amino acids of the intracellular domain (Bennett et al., 1995; Bergemann et al., 1995). Using the intracellular domain in yeast two-hybrid screens, several binding proteins have been identified (Torres et al., 1998; Bruckner et al., 1999; Lin et al., 1999). All the binding proteins identified to date contain a PDZ (PSD-95/Dlg/ZO-1) domain, a protein module that binds the C-termini of membrane proteins. PDZ proteins have been widely implicated in forming sub-membrane scaffolds that cluster molecules at the cell surface (Craven and Bredt, 1998; Garner et al., 2000; Sheng and Pak, 2000).

RGS proteins form a large molecular family identified in recent years, with more than 20 members in mammals (Arshavsky and Pugh, 1998; Kehrl, 1998; De Vries and Farquhar, 1999; Zheng et al., 1999). They act as GTPase activating proteins (GAPS) for heterotrimeric G proteins, accelerating the G protein catalytic cycle and thereby facilitating rapid signaling processes such as retinal phototransduction (Arshavsky and Pugh, 1998). Many RGS proteins contain additional motifs, including PDZ domains, leading to suggestions that they could couple G proteins with other signaling pathways (Kehrl, 1998; De Vries and Farquhar, 1999). The RGS protein pl15RhoGEF has separate domains that regulate both heterotrimeric and small G proteins, while nematode EAT-16 mediates a genetic interaction between two heterotrimeric G protein pathways (Hart et al., 1998; Kozasa et al., 1998; Hajdu-Cronin et al., 1999). However, there is generally little functional evidence on the specific significance of combining RGS domains with other domains, including a potential role for PDZ-RGS proteins in regulating G proteins in response to extracellular signals.

Heterotrimeric G protein-coupled receptors (GPCRs) are seven-transmembrane proteins that mediate the effects of many extracellular signals (Watson and Arkinstall, 1994; Bargmann and Kaplan, 1998). Some of the best characterized guidance molecules act through GPCRs (Parent and Devreotes, 1999), notably the chemokines, which are leukocyte chemoattractants with important roles in immunity (Melchers et al., 1999). A role for chemokines in neural development was shown more recently. The radial movement of cerebellar granule cells is a well characterized model for neural migration (Rakic, 1990; Hatten, 1999) and occurs prematurely in mice with gene disruptions of the chemokine SDF-1, or its receptor CXCR4 (Ma et al., 1998; Zou et al., 1998). Heterotrimeric G protein signaling may also mediate, at least in part, the actions of Netrins, Semaphorins and other neural guidance molecules, though these pathways are generally less well understood (Vancura and Jay, 1998; Corset et al., 2000; Nakamura et al., 2000).

SUMMARY OF THE INVENTION

In one aspect, an embodiment of the invention provides an amino acid sequence having a PDZ domain and an RGS domain. An embodiment of the invention is a protein comprising an amino acid sequence substantially identical to that shown in SEQ ID NO: 1. Further, an embodiment of the invention is a nucleic acid encoding the amino acid sequence of the protein. The nucleic acid is an isolated nucleotide sequence encoding the amino acid sequence of the protein. Further, a nucleic acid that hybridizes to this nucleic acid is provided, as is a recombinant vector, and a recombinant cell containing the vector, comprising any of these nucleic acids. In one embodiment, the protein is encoded by a gene from a vertebrate, for example, the vertebrate is a mammal.

In a further aspect, an embodiment of the invention is a protein encoded by a gene, the protein having an RGS domain and a PDZ domain, the PDZ domain being capable of binding to a portion of a cytoplasmic domain of an ephrin-B2 in a cell. For example, the binding occurs in a two-hybrid system in a yeast cell, wherein the ephrin-B2 cytoplasmic domain is used as the bait of the system. Further, the mammalian cDNA library is obtained from a tissue selected from the group consisting of an embryo, a tumor or a leukemia, for example, the tumor is of neural origin, for example, the tumor of neural origin is a neuroblastoma.

In a further aspect, an embodiment of the invention is a protein having an RGS domain and a PDZ domain or a protein comprising an amino acid sequence substantially identical to that shown in SEQ ID NO: 1, wherein the protein causes stimulation of ephrin-B1 induced de-adhesion of embryonic test cells at levels of ephrin-B1 that are suboptimal, for example, when the stimulation is at least 2-fold, for example at least 4-fold, or at least 8-fold. Further, the stimulation is dependent on the presence of an amino acid sequence present in the carboxy terminal RGS domain, or the stimulation is reversed in a dose-dependent manner in the presence of the amino terminal PDZ domain and in the absence of the carboxy terminal RGS domain. Further, the embryonic test cells are from an embryo of a cold-blooded vertebrate, for example, the vertebrate is an amphibian.

In a further aspect, an embodiment of the invention is a soluble eph2 receptor capable of binding a cell, such that a pattern of migration of the cell is altered.

In a further aspect, an embodiment of the invention is a method of altering sensitivity of a cell to a chemokine, comprising: transmitting a reverse signal from a recombinant soluble ephB2 receptor to a transmembrane protein in the cell which is a ligand of the ephB2 receptor; binding a cytoplasmic protein, the cytoplasmic protein having an RGS domain and a PDZ domain, to the cytoplasmic domain of the transmembrane protein in the cell; and altering a reaction of a G-protein coupled receptor (GPCR) in the membrane of the cell, such that the cell has altered sensitivity to a chemoattractant chemokine. Further, the cell is selected from the group of: a leukocyte; a granule cell located in an external granule cell layer (EGL) of a developing brain cerebellum; a cell involved in migration, blood vessel formation, axon pathway selection, or rhombomere compartmentation. The transmembrane protein is substantially homologous to an ephrin-B2, or transmission of the reverse signal requires a presence of the PDZ-RGS3 protein in the first cell, or the chemokine is an SDF-1, for example, transmission of the reverse signal causes loss of responsiveness of the cell to the SDF-1. Further, when the cell is a leukocyte, the method by which the cell loses sensitivity to the chemokine is a treatment for an inflammatory condition or an autoimmune disease. Further, an embodiment of the invention provides omitting the recombinant soluble ephB2 and screening the sample for a chemical agent that substitutes functionally for the omitted ephB2, the method comprising adding a test sample to screen the sample for the presence of the agent that alters sensitivity of the cell to the chemokine.

In a further aspect, an embodiment of the invention is a method of modulating an intracellular pathway involved in cell migration upon the event of a cell to cell contact, comprising: initiating ephrin signaling by providing cell to cell contact in a cell having a cytoplasmic protein, the cytoplasmic protein having an amino terminus that interacts with the carboxy terminus of ephrin, and having a carboxy terminus that affects a GTP-linked reaction of a seven transmembrane protein, causing the cell in the presence of sufficient chemokine to otherwise inhibit such migration from an initial anatomical location and towards a target location. Further, the method involves selecting the cell from a group consisting of a granule cell and a leukocyte, such that the protein mediates an intracellular pathway that causes the granule cell to migrate away from the EGL, or that causes the leukocyte to migrate into an inflamed tissue, respectively.

In a further aspect, an embodiment of the invention is a method of screening for the presence in a test sample of an agent that alters in vivo functional interactions among the components of an ephrin-B signal pathway involving chemoattraction by a chemokine, comprising: placing chemokine-sensitive cells having the ephrin-B ligand on a top side of a filter in an upper chamber of a transwell system, wherein the filter has pores of uniform size and separates the upper chamber from a lower chamber, and wherein the lower chamber contains the chemokine; adding a test sample to the lower chamber; and analyzing the lower side of the filter to determine an amount of migration of the cells into the lower chamber. Further, the method comprises having a second transwell such that adding a test sample to the lower chamber of the second transwell is omitted as a control, and further comparing the amount of migration of cells in the presence and absence of the test sample is an indication of the effect of the agent on cell migration. Further, the cells are selected from a purified preparation of cerebellar granule cells and a pure cultured leukocyte cell line; further, the chemokine can be SDF-1. Further, the lower chamber contains the chemokine at a sub-optimal level, wherein the agent in the test sample causes a decrease in cell migration in comparison to the second transwell control. The agent is an anti-inflammatory or an anti-autoimmune therapeutic composition. Further, the agent causes a increase in cell migration in comparison to the control, for example, the agent is a novel chemokine, or the agent is a low molecular weight synthetic organic chemical.

In other embodiments according to the claimed invention, a pharmaceutical composition is described for delivering to a selected site an effective dose of a protein having an RGS domain and a PDZ domain capable of altering the sensitivity of a cell to a chemokine comprising an effective dose of said protein and a suitable carrier, and optionally additional active or inert ingredients such as diluents, stabilizers, and excipients.

Another embodiment in accordance with the present invention includes a pharmaceutical composition for delivering to a selected site an effective dose of a protein having an RGS domain and a PDZ domain capable of altering the sensitivity of a cell to a chemokine comprising an effective dose of said protein and a suitable carrier, and optionally additional active or inert ingredients such as diluents, stabilizers, and excipients, wherein the pharmaceutical composition is administered intradermally, intramuscularly, subcutaneously, topically, or in the form of a vector. In addition, the presently claimed invention describes a pharmaceutical composition as above further comprising a substance that allows for the slow release of the pharmaceutical composition at the selected site. Still yet another embodiment in accordance with the present invention is a pharmaceutical composition as above wherein the selected site for delivery is a tumor site, or an allergic response site, or an autoimmune response site.

Another embodiment in accordance with the present invention is a viral vector comprising the nucleic acid sequence encoding the protein of SEQ ID NO.1. And another embodiment in accordance with the present invention is a plasmid comprising the nucleic acid sequence encoding the protein of SEQ ID NO.1.

BRIEF DESCRIPTION OF THE DRAWINGS

The foregoing features of the invention will be more readily understood by reference to the following detailed description, taken with reference to the accompanying drawings, in which:

FIG. 1A shows the domain structure of mouse PDZ-RGS3. Human RGS3 is diagrammed below.

FIG. 1B is a dendrogram showing sequence homologies among representative human and mouse RGS proteins. For relationships with additional proteins, see Zheng et al. (1999). The Clustal program was used to align the RGS domains.

FIG. 1C is the amino acid sequence of mouse PDZ-RGS3 is deduced from the cDNA nucleotide sequence. PDZ and RGS domains are boxed. The human RGS3 sequence is aligned, with identical amino acids indicated by shading.

FIG. 2A is a GST fusion protein pull-down assay. GST-ephrin-B1 affinity beads were incubated with 35S-labeled PDZRGS3 or mutant derivatives. Bound proteins were resolved on SDS gel and autoradiographed. GST fusion protein on the affinity beads was Coomassie blue stained to ensure similar amounts (lanes 10 and 11).

FIG. 2B shows co-immunoprecipitation from transfected cells. HA-tagged ephrin-B1 and myc-tagged PDZ-RGS3 were co-transfected into COS cells. Cell lysates were immunoprecipitated with anti-HA or anti-myc antibody. After Western blot, each membrane was cut into an upper half with proteins above 80 kDa, probed with anti-myc antibody to detect myc-PDZ-RGS3 or myc-SAP97, and the lower half probed with anti-ephrin-B.

FIG. 2C shows co-immunoprecipitation of endogenously expressed PDZ-RGS3 and ephrin-B1. Lysates of CHP100 neuroblastoma cells (lane 1) or mouse cerebral cortex (lanes 2 and 3) were immunoprecipitated with anti-ephrin-B1 A20 antibody (lanes 1 and 2) or control rabbit immunoglobulin (lane 3). Immunoprecipitates were Western blotted and probed with anti-PDZ-RGS3. PDZ-RGS3 expressed by transfection in 293T cells was used as a marker (lane 4).

FIG. 2D shows co-localization of staining in transfected COS cells (examples arrowed). Cells were co-transfected with myc-PDZ-RGS3 and HA-ephrin-B1, then permeabilized and immunostained with anti-ephrin-B and anti-myc.

FIG. 3A shows Ephrin-B1 localization in parasagittal sections of the brain in the ventricular zone (VZ) of the cerebral cortex.

FIG. 3B shows PDZ-RGS3 localization in parasagittal sections of the brain in the ventricular zone (VZ) of the cerebral cortex.

FIG. 3C shows Ephrin-B2 localization in parasagittal sections of the brain in the cerehellar primordium (CP).

FIG. 3D shows PDZ-RGS3 localization in parasagittal sections of the brain in the ccrebellar primordium (CP).

FIG. 3E shows Ephrin-B1 and B2 localization in parasagittal sections of whole embryo in dorsal root ganglia (DRG).

FIG. 3F shows PDZ-RGS3 localization in parasagittal sections of whole embryo in the dorsal root ganglia (DRG).

FIG. 5A shows localization of RNAs for ephrin-B2, EphB2, SDF-1 and CXCR4 using in situ hybridization in parasagittal sections of mouse brain at the postnatal stages indicated. Migration of cerebellar granule cells inward from the EGL begins around P3. SDF-1 expression is seen in the pial membrane overlying the cerebellum, while its receptor CXCR4 shows expression in the cerebellar EGL, at P0 and P3. Expression of ephrin-B2 and its receptor EphB2 is low or undetectable at P0 but is seen clearly in the EGL at P3.

FIG. 5B shows immunofluorescence of purified cerebellar granule cells. Cells are stained with EphB2-Fc, or with antibodies to CXCR4, PDZ-RGS3, or ephrin-B (antibody C18, which recognizes ephrin-B1 or -B2), or control rabbit immunoglobulin. The top two panels show the same cell stained with different fluorochromes.

FIG. 5C shows purified granule cells treated unfixed with EphB2-Fc receptor fusion protein, then fixed, permeabilized and stained with anti-PDZ-RGS3 (red) and anti-Fc (green). Patches on the cell body and cell processes show co-staining (examples indicated by arrowheads and arrows).

FIG. 6A shows chemotaxis of granule cells to SDF-1 placed in the lower chamber. This chemotaxis is inhibited by EphB2-Fc placed in the upper chamber. EphB2-Fc by itself, here placed in the upper chamber, has no detectable effect. Control Fc does not block granule cell chemotaxis to SDF-1.

FIG. 6B shows chemotaxis of granule cells to BDNF placed in the lower chamber. EphB2-Fc does not inhibit chemotaxis to BDNF.

FIG. 6C shows the effect of PDZ-RGS3$^{PDZ-EGFP}$ on chemotaxis. PDZ-RGS3$^{PDZ-EGFP}$, a dominant negative truncated form of PDZ-RGS3, was fused to an EGFP fluorescent marker and introduced into purified cerebellar granule cells using a Sindbis viral vector. Fluorescently labeled granule cells expressing PDZ-RGS3$^{PDZ-EGFP}$ still show chemotaxis to SDF-1, but the inhibitory effect of EphB2-Fc on chemotaxis is now blocked.

FIG. 7A shows a molecular model for reverse signaling through B ephrins. Binding of B ephrins and their EphB receptors results in bi-directional signaling. Heterotrimeric G protein signaling is activated by ligands that act through seven transmembrane receptors, such as the chemoattraciant SDF-1 and its receptor CXCR4. PDZ-RGS3 binds the cytoplasmic C-terninus of B ephrins through its PDZ domain, and inhibits heterotrimeric G protein signaling through the GAP activity of its RGS domain. These interactions provide a link between ephrin reverse signaling and G protein coupled chemoattraction.

FIG. 7B shows regulation of chemoattraction by EphB2 reverse signaling. Purified cerebellar granule cells are chemoattracted to either SDF-1 or BDNF. EphB2-Fc inhibits the response to SDF-1, providing a mechanism for selective regulation of responsiveness to guidance factors.

DETAILED DESCRIPTION OF SPECIFIC EMBODIMENT

Figure 1:
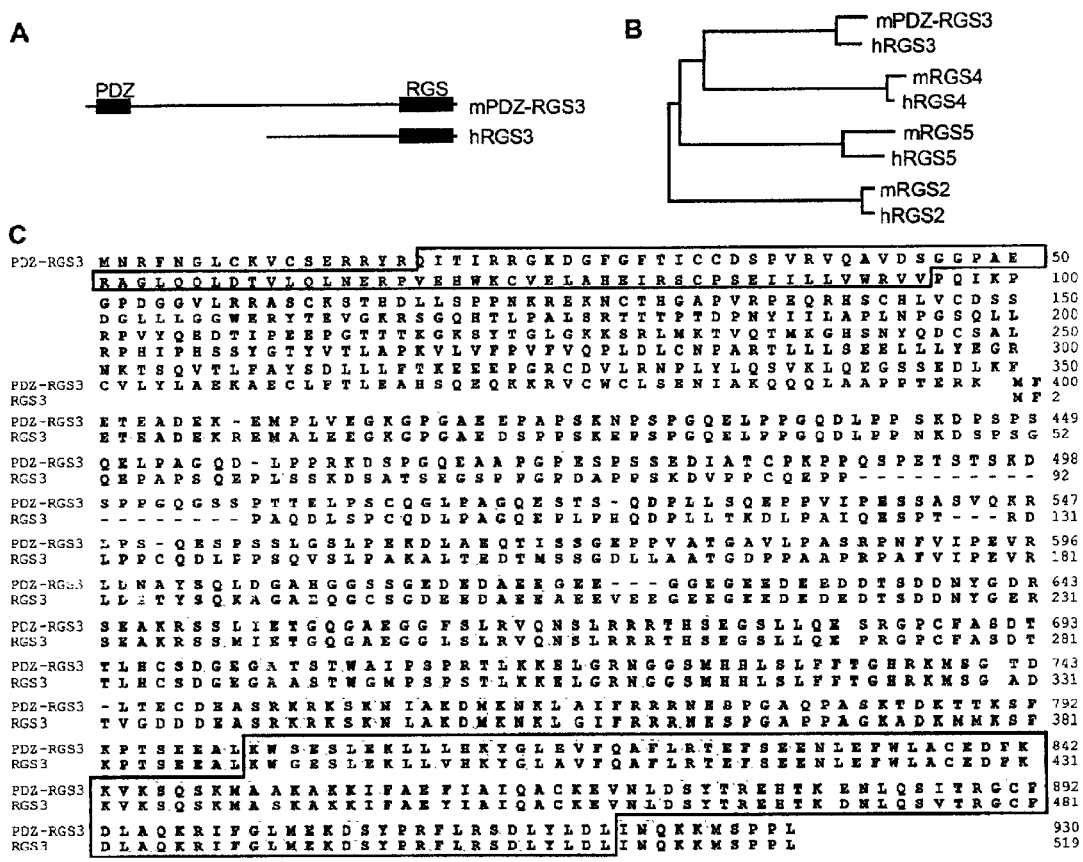
FIG. 1 is a general overview of the primary structure of PDZ-RGS3.

All references cited herein are incorporated in their entirety by reference.

Definitions. As used in this description and the accompanying claims, the following terms shall have the meanings indicated, unless the context otherwise requires: Chemokine refers to small molecular weight proteins that regulate leukocyte migration and activation. They are typically secreted by activated leukocytes themselves, and also by stromal cells such as endothelial and epithelial cells, after inflammatory stimuli. Examples of chemokines include monocyte chemotactic protein (MCP)-3, MCP-4, macrophage inflammatory protein (MIP)-1α, MIP-1β, RANTES (regulated on activation, normal T cell expressed and secreted), SDF-1, Teck (thymus expressed chemokine), and MDC (macrophage derived chemokine). As used herein, chemokine also includes any molecule that can act as a chemotactic agent. A chemotactic agent may be a small chemical compound, natural or synthetic, that is a selective agonist of a chemokine receptor, for example, CXCR4, a heterotrimeric G protein-coupled receptor (GPCR) that is the receptor for the chemoicine SDF-1.

Altered cell migration means, within the context of the present invention, a measurable or observable effect on cell migration by an agent, when compared to cell migration in the absence of said agent.

Altered sensitivity to a chemokine means, within the context of the present invention, an effect of a chemokine on a population of cells that is measurably or observably different under one set of conditions (for example, in the absence of a PDZ-RGS3 protein) from the effect of the same chemokine on the same population of cells under a different set of conditions (for example, in the presence of a PDZ-RGS3 protein).

Chemokine-sensitive cell means a cell that shows a measurable or observable response to a chemokine, as defined above, in the context of cell migration.

A low molecular weight synthetic organic molecule means, within the context of the present invention, a synthetic chemokine.

Little is known of the specific effects of B ephrin reverse signaling on individual cells, or the signal transduction pathways that lead to such effects. The inventors have recently identified PDZ-RGS3 as a binding partner of B ephrins. In a Xenopus embryo de-adhesion assay, PDZ-RGS3 mediates signaling by the B ephrin cytoplasmic tail, in a manner dependent on both PDZ and RGS domains. Identification of the RGS protein led to further studies that identified a relationship between ephrins and chemokines. The inventors found that both SDF-1 and BDNF are in vitro chemoattractants for cerebellar granule cells. SDF-1 chemoattraction is selectively inhibited by soluble EphB receptor, and this inhibition is blocked by a truncated PDZ-RGS3 lacking the RGS domain. These results demonstrate a pathway connecting B ephrins to regulation of G protein coupled chemoattraction, and lead to a model for regulation of migration in cerebellar development.

Cell biological effects, and molecular mechanisms of ephrin-B reverse signaling, were characterized. In the course of their investigations, the inventors uncovered a novel pathway for extracellular control of heterotrimeric G proteins, and demonstrated selective regulation of responsiveness to guidance factors as a mechanism that can regulate neuronal migration.

Chemoattraction of a cell to another by chemokine stimuli can be modulated and/or regulated in cells by treatment with a PDZ-RGS3 type protein, wherein the PDZ-RGS3 type protein binds to a transmembrane protein such as B-ephrin, altering the cell's sensitivity to the chemokine. In the context of immune reactions such as autoimmune disease, tissue rejection or allergy, the invention provides compositions and methods for altering leukocyte sensitivity to chemokines involved in such immune responses.

Modulation of chemokine signaling may also occur through the blocking of chemotaxis by ephrin reverse, and possibly forward, signaling. In such a pathway, soluble proteins comprising Eph receptor ectodomains may stimulate signaling through Eph receptors and interaction with the highly conserved PDZ-binding motifs. PDZ domains of various cell molecules including chemokines are known to also interact with the conserved PDZ-binding motifs. Introduction of soluble Eph receptor fusion proteins might thereby block the effect of chemokines or other G-protein coupled pathways involving molecules with PDZ domains that bind to the conserved PDZ-binding domains of the membrane proteins.

It has also recently been shown that tumor cells express a distinct, non-random pattern of functionally active chemokine receptors (Möller, et al., Nature, 410, 50 (2001)). In vitro, chemokine ligand-receptor interactions trigger intracellular actin polymerization in leukocytes, a process that is prerequisite for cell motility and migration. Consistent with findings in leukocytes, CXCL12 (100 nM) and CCL21 (100 nM) induced, respectively, a transient 2.2- and 1.6-fold increase in intracellular filamentous actin (F-actin) in human breast cancer cells within 20 s. Conversely, the chemokine $CX_3CL1$/fractalkine, whose receptor $CX_3CR1$/V28 was not detected on breast cancer cells, did not induce actin polymerization.

In tumor cells, high levels of actin polymerization are required for the formation of pseudopodia, which in turn are needed for the invasion of malignant cells into tissues and for efficient metastases formation. Confocal laser scan microscopy of breast cancer cells stimulated in suspension with either CXCL12 or CCL21 revealed intense F-actin staining in the periphery of the cells and a redistribution of F-actin towards a leading edge. In adherent breast cancer cells, distinct pseudopodia formation was observed after min of stimulation with either CCL21 or CXCL12.

In agreement with these findings, both CXCL12 and CCL21 induced directional migration of breast cancer cells and directional invasion through a reconstituted basement membrane in a dose-dependent manner. Optimal migratory/invasive responses to CXCL12 or CCL21 were observed at concentrations of 100 nM, or 100 and 200 nM, respectively, reminiscent of observations made with leukocytes. Compared with breast cancer cells of well-characterized cell lines (MDA-MB-231, MDA-MB-361), primary tumor cells derived from a patient with malignant pleural effusion exhibited significant chemotactic responses to both CXCL12 and CCL21. CXCL12- and CCL21-mediated chemotaxis and invasion could be blocked by neutralizing anti-CXCR4 or anti-CCL21 antibodies, respectively, confirming the specificity of the chemotactic response induced by these chemokines.

Thus, signaling through CXCR4 or CCR7 mediates actin polymerization and pseudopodia formation in breast cancer cells, and induces chemotactic and invasive responses. In addition, it was found that organs representing the main sites of breast cancer metastasis are the most abundant sources of ligands for these tumor-associated receptors. In vivo, neutralizing the interactions of CXCL12/CXCR4 leads to a significant inhibition of lymph-node and lung metastasis.

In accordance with one embodiment of the present invention, there is provided a pharmaceutical composition comprising a soluble protein having an Eph receptor for delivering to a selected site an effective dose of said soluble protein, a suitable carrier, and optionally additional active or inert ingredients such as diluents, stabilizers, and excipients said soluble protein being capable of altering a cell signaling pathway. The pharmaceutical composition is then administered to a patient with cancer, for inhibiting cell response pathways involving chemokine-mediated mechanisms in tumor metastasis.

The protein used in practicing the claimed invention may be a recombinant protein with an amino acid sequence identical to the claimed sequence of SEQ ID NO. 1, or a recombinant protein derived from SEQ ID NO. 1 but including modifications that change its pharmokinetic properties while keeping its original B ephrin-(PDZ-) binding domain and its regulator of heterotrimeric G protein signaling-(RGS-) domain. The protein may also be a soluble protein or fusion protein of the Eph receptor domain comprising the conserved 33 amino acids of the C-terminus of the B ephrins—the PDZ-binding motif, a motif also found in many other cell surface molecules.

The mode of delivery of the protein may be by injection, including intradermal, to intramuscular and subcutaneous, or topical, such as an ointment or patch. The protein may also be delivered as a nucleic acid sequence by way of a vector, such as a viral vector (e.g. adenoviruse, poxvirus, retrovirus, lentivirus, or a Sindvis viral vector), or an engineered plasmid DNA.

Generally, the proteins of the presently claimed invention are administered as pharmaceutical compositions comprising an effective dose of the PDZ-RGS type protein or soluble Eph receptor domain in a pharmaceutical carrier. The protein can be combined for therapeutic use with additional active or inert ingredients, such as in conventional pharmaceutically acceptable carriers or diluents, along with physiologically innocuous stabilizers and excipients. A pharmaceutical carrier can be any compatible, non-toxic substance suitable for delivering the compositions of the claimed invention to a patient The quantities of reagents necessary for effective therapy will depend upon many different factors, including means of administration, target site, physiological state of the patient, and other medicaments administered. Thus, treatment dosages should be titrated to optimize safety and efficacy. Animal testing of effective doses for treatment of particular cancers or disease states such as autoimmune or allergic response will provide further predictive indication of human dosage. Pharmaceutically acceptable carriers will include water, saline, buffers, and other compounds described, for example, in the Merck Index, Merck & Co., Rahway, N.J. Slow release formulations, or a slow release apparatus may be used for continuous administration.

Dosage ranges for the claimed proteins would normally be expected to be in amounts lower than 1 mM concentrations, typically less than about 10 µLM concentrations, usually less than about 100 nM, and particularly less than about 10 pM and more particularly less than about 1 fM, with an appropriate carrier. Treatment is normally initiated with smaller dosages which are less than optimum, and from there, the dosage is increased by small amounts to achieve the optimum effect under the circumstances. Determination of the ideal dosage and administration protocol for a particular patient or situation will be readily identified by one with ordinary skill in the art.

It has been shown by the inventors that a cytoplasmic protein containing a PDZ idomain and an RGS domain is capable of binding to B ephrins through the PDZ domain and mediating signaling from the cytoplasmic tail of the B ephrin. The signal mediation is dependent on both the PDZ and the RGS domains. Chemokines such as SDF-1, also known as SDF-1α, and BDNF, typically associated with leukocyte migration, herein act as chemoattractants for cerebellar granule cells. The inventors found that the chemokine SDF-1 is selectively inhibited by the presence of soluble EphB receptor but that this inhibition is blocked by a truncated PDZ-RGS type protein lacking the RGS domain, suggesting a connection between B ephrins and regulation of G protein-coupled chemoattraction. Effects of the presently claimed proteins on immune response or cell migration could be monitored by a number of different methods. For example, measuring an immune response, whether enhanced or inhibited, to antigen-specific stimulation of imnmunoglobulin levels in serum, typically known as B-cell response, could be done in the presence or absence of the claimed proteins. In addition, a similar analysis for an increase or decrease in specific immunoglobulins associated with T cells is possible.

In accordance with one embodiment of the present invention, the proteins claimed s herein could be used in cancer treatment, or to treat autoimmune and/or allergic responses and diseases. An altered immune response is thus measured or observed by analyzing an antigen-specific cytotoxic response of defined population of lymphocytes such as those of the blood, spleen, lymph nodes, or a tumor. Other means for monitoring the effect of a PDZ-RGS type protein include analysis of rates of tumor metastasis, or tumor growth, or lo an increase or decrease in tumor incidence in a patient or animal model or cell population.

Additional diseases or medical conditions envisioned to be appropriate systems for monitoring altered cell migration such that ephrin signaling will provide therapeutic benefit in inflammatory and autoimmune diseases include: arthritis (including iosteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), Huntington's disease, Parkinson's disease, migraine, depression, peripheral neuropathy, pain, cerebral amyloid angiopathy, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock, and other conditions characterized by hyperinflammatory states and autoimmune dysfunctions.

In accordance with one embodiment of the present invention, the proteins or protein fragments claimed herein could be formulated alone or in combination with substances for slow release at a delivery site. Alternatively, they could be formulated as fusion proteins or constructs made by chemical ligation of a PDZ-RGS type protein or protein fragment and a targeting moiety, or of an Eph receptor ectodomain type protein and a targeting moiety, thus allowing delivery of the construct to tumors of interest (for example, the targeting moiety could be an antibody or fragment of antibody, or a protein ligand, or a peptide of more than about 10 amino acids). Similarly, they could be formulated as a DNA or viral vector (for example, a Sindvis vector) encoding the protein or protein fragment with or without a targeting moiety.

EXAMPLES

The claimed invention may be illustrated by the following non-limiting examples, which are more easily understood by reference to the following experimental details.

Plasmids and Antibodies

GST fusions were in vector pGEX2T (Pharnacia), and plasmids for cell transfection or embryo injection in vector CS2(+) (Rupp et al., 1994). In situ probes were: full length ephrin-B1 cDNA (Davis et al., 1994); XbaI/XhoI fragment of ephrin-B2 (Bergemann et al., 1995); nucleotides 3 to 861 of PDZ-RGS3; HindIII/PstI fragment of ephrin-B3 (Bergemann et al., 1998); nucleotides 2698 to 3104 of EphB2 (Henkemeyeret al., 1996); nucleotides 2139 to 2873 of EphB3 (Ciossek et al., 1995); or CXCR4 and SDF-1 probes as described (Suzuki et al., 1999). Myc-SAP97 and myc-PSD95 plasmids were gifts from Dan Pak and Morgan Sheng. Rabbit polyclonal anti-PDZ-RGS3 antibodies were raised against an internal peptide TIPEEPGTTTKGKSYT (SEQ.ID no. 5) or the C-terminal peptide RSDLYLINQKKMSPPL (SEQ.ID no. 6), with an N-terminal cysteine added for conjugation with carrier KLH. Antiserum was affinity purified on peptide columns using SulfoLink kit (Pierce). Antibodies to both peptides detect PDZ-RGS3 in Western blots of transfected cells and tissues. Rat monoclonal anti-HA was from Boehringer Mannheim. Mouse monoclonal anti-Myc, rabbit anti-ephrin-B1 (A20), rabbit anti-ephrin-B (C18) and goat anti-CXCR4 (C20) were from Santa Cruz Biotechnology.

Yeast Two-hybrid Screen and cDNA Cloning

A two-hybrid library, a gift from Stanley Hollenberg, was screened as described (Hollenberg, et al., 1995). Several clones with overlapping partial sequences of PDZ-RGS3 were obtained. The longest contained nucleotides 15 to 465 and was used to probe a mouse newborn brain cDNA library (Stratagene). Among several overlapping clones, the longest contained nucleotides 1 to 1421. To obtain full length cDNA, 3' RACE was performed on mouse E15.5 Marathon cDNA (Clontech) using 5' internal primer set gtgggcaagcg-cagtggccagcacaccctg (SEQ.ID no. 3) and ccgcacatcccgcat-tccagttacggcacc (SEQ.ID no. 4). Multiple RACE clones were sequenced to ensure fidelity.

GST Pull-down, Immunoprecipitation and Western Blot

GST fusions expressed in strain BL21 were immobilized on glutathione beads (Sigma). Twenty-five-pL beads were incubated with 25–50 $\mu L^{35}$S-labeled PDZ-RGS3 made by in vitro transcription and translation (Promega TNT kit), in 500 µL binding buffer (25 mM TrisHCl 7.4, 150 mM NaCl, 1 mM EDTA and 1 mM DTF). Beads were washed with binding buffer followed by SDS-PAGE and autoradiography.

For immunoprecipitations, COS cells were Lpofectamine transfected (Gibco) and lysed 30 hr later (25 mM Tris-HCl 7.4, 150 mM NaCl, Boehringer protease inhibitor cocktail, 1 mM DTT and 1% Triton X-100). After-microfuge clearing, supernatants were incubated with antibodies 1 hr, then protein A sepharose beads (Pharmacia) 1 hr. Beads were washed with lysis buffer, proteins were resolved on SDS gels, and transferred to PVDF membranes (Gelman Sciences).

Mouse E16.5 cerebral cortices were triturated with a blue Gilson tip in hypotonic buffer (25 mM Tris-HCl 7, protease inhibitor cocktail, 1 mM DTT). After 10 min on ice, cells were lysed by passing through a 27-gauge needle 4–6 times. After microfuging 5000 rpm, 5 min, supernatant containing membranes and cytosol was incubated with 1% Triton X-100, 150 mM NaCl, 10 min on ice before immunoprecipitation as above.

Xenopus Embryo De-adhesion and Granule Cell Migration Assays

For the *Xenopus* assay, plasmids were NotI linearized and transcribed to capped mRNA by SP6 mMessage mMachine kit (Ambion). Two-cell embryos were injected, and screened for dc-adhesion as described (Jones et al., 1998). For each plasmid combination, protein levels were tested by Western blot and were consistent. Approximately 30 embryos were tested for each condition in each experiment, and experiments were repeated 3 to 5 times with consistent results. Data shown are averages of all results combined.

For migration assays, granule cells from P8-P9 mouse cerebella were dissociated and purified as described (Hatten, 1985) with modifications. Briefly, the cell suspension was spun 20 min, 3500 rpm on a step gradient (60% and 35% isotonic Percoll). The second layer of cells was collected, washed, and resuspended in NB medium (Neurobasal/B27; Gibco). Purified cells were incubated 37° C. on a poly-D-lysine coated culture flask, then shaken off after 2 hr for the migration assay. The cells were found to need this recovery period, perhaps for restoration of ephrin-B1 expression after trypsin cleavage.

Transwell membranes (polycarbonate, 5 micron pores; Costar) were pre-coated on both sides with laminin (20 µg/mL)·1 hour then PBS washed. BDNF (Peprotech), SDF-1 (also called SDF-1α; Peprotech or Calbiochem) and EphB2-Fc were found most effective at concentrations of 10 ng/mL, 100 ng/mL, and 2 µg/mL, respectively, in line with previous publications. 100,000 cells were placed in the top chamber and incubated 37° C., 5% C02, 16 hr. The membrane was then methanol fixed and Giemsa stained. The upper side was wiped off, and cells that had migrated and attached to the lower side were counted blind, in 4 central fields with a 16× objective. Each condition was tested in duplicate or triplicate per experiment, and each experiment repeated 3 to 5 times with consistent results. Data shown are averages of all results combined.

For viral transduction, PDZ-RGS3$^{PDZ-EGFP}$ was cloned into pSinRep5 (Invitrogen), and virus produced by the manufacturer's instructions. Immediately after the 2 hr recovery of purified granule cells, EGFP or PDZ-RGS3$^{PDZ-EGFP}$ virus, with a similar titer, were added. Infection was 1 hr, room temperature on an orbital shaker, then 1 hr at 37° C. The assay was as above, except migration was for only 6 hr, then membranes were fixed with 4% paraformaldehyde in PBS 10 min, washed once with PBS, and slide mounted with fluoromount-G (Southern Biotechnology).

Immunocytochernistry

COS cells transfected with HA-ephrin-B1 and myc-PDZ-RGS3 were fixed in 4% paraformnaldehyde, 4% sucrose in PBS, incubated with C18 antibody and monoclonal anti-myc in 0.5% NP40, 5%BSA in PBS, 1 hr, then secondary antibodies for 1 hr (donkey anti-rabbit-Rhodamine RedX and donkey anti-mouse-FITC; Jackson Immunoresearch) and mounted in Fluoromount-G.

Purified granule cells were cultured overnight on laminin (100 µg/mL) pre-coated coverslips. EphB2-Fc (5 µg/) was added, 30 min, 37° C. Cells were fixed 15 min in 4% parafonnaldehyde, 4% sucrose in PBS, permeabilized 5 min, 0.25% Triton)X-100, blocked 2 hr, 10% BSA in PBS, labeled 4° C. overnight with rabbit anti-human Fc plus goat anti-CXCR4, or goat anti-human Fc (Jackson lmmunoresearch) plus rabbit anti-PDZ-RGS3 in 3% BSA in PBS, then 2 hr, room temperature with secondary antibodies (donkey anti-goat-FITC and donkey anti-rabbit-Rhodamine RedX) and mounted in ProLong Antifade (Molecular Probes).

Immunocytochemistry using purified leukocyte cells is done as with granule cells. The purified leukocytes are cultured overnight, using standard techniques known to those skilled in the art. Addition of EphB2-Fc and labeling with anti-human Fc plus goat anti-CXCR4, or goat-anti-human FC plus rabbit anti-PDZ-RGS3 with secondary antibodies is as described above for granule cells.

Example 1

Investigation of Reverse Signaling by B Ephrin
Identification of B Ephrin Binding Proteins As a first step to dissect reverse signaling, identification of B ephrin binding proteins was undertaken. Yeast two-hybrid cloning was employed, screening a mouse embryonic cDNA library (Hollenberg, et al., 1995) with the entire cytoplasmic domain of ephrin-B2 as bait. Subsequent studies focused on one of the cDNAs identified, encoding a previously unidentified 930 amino acid protein sequence (FIG. 1). Two motifs were identified in this sequence, a PDZ domain at the N-terminus, and an RGS domain at the C-terminus. The initial screen identified a subfragment containing the PDZ domain, and the rest of the cDNA was then assembled by library screening and polymerase chain reaction (see experimental detail, above). The linkage of PDZ and RGS domains in the same molecule in mouse tissues was confirmed by Northern blot, Western blot and in situ hybridization (experimental procedures and data not shown).

Database searching revealed no identical sequence. However, it did reveal strong homology of the C-terminal half of this mouse sequence to human RGS3, which was previously described as a shorter sequence (FIG. 1). Like human RGS3 (Druev et al., 1996), the PDZ-RGS protein identified here can inhibit G protein mediated MAP kinase activation in transfected cells (data not shown) confirming its GAP activity. While it is not known definitively whether the mouse and human proteins have a direct ortholog relationship, in view of the close homology within their RGS domains the newly identified protein has been called PDZ-RGS3.

Binding of PDZ-RGS3 to B Ephrins

After identifying PDZ-RGS3, the results of the two-hybrid screen were investigated to determine whether they reflect a biologically meaningful interaction. To address this, binding between PDZ-RGS3 and B ephrins was tested, using several approaches.

1. In Vitro GST Fusion Protein Pull-down Assay.

Figure 2:
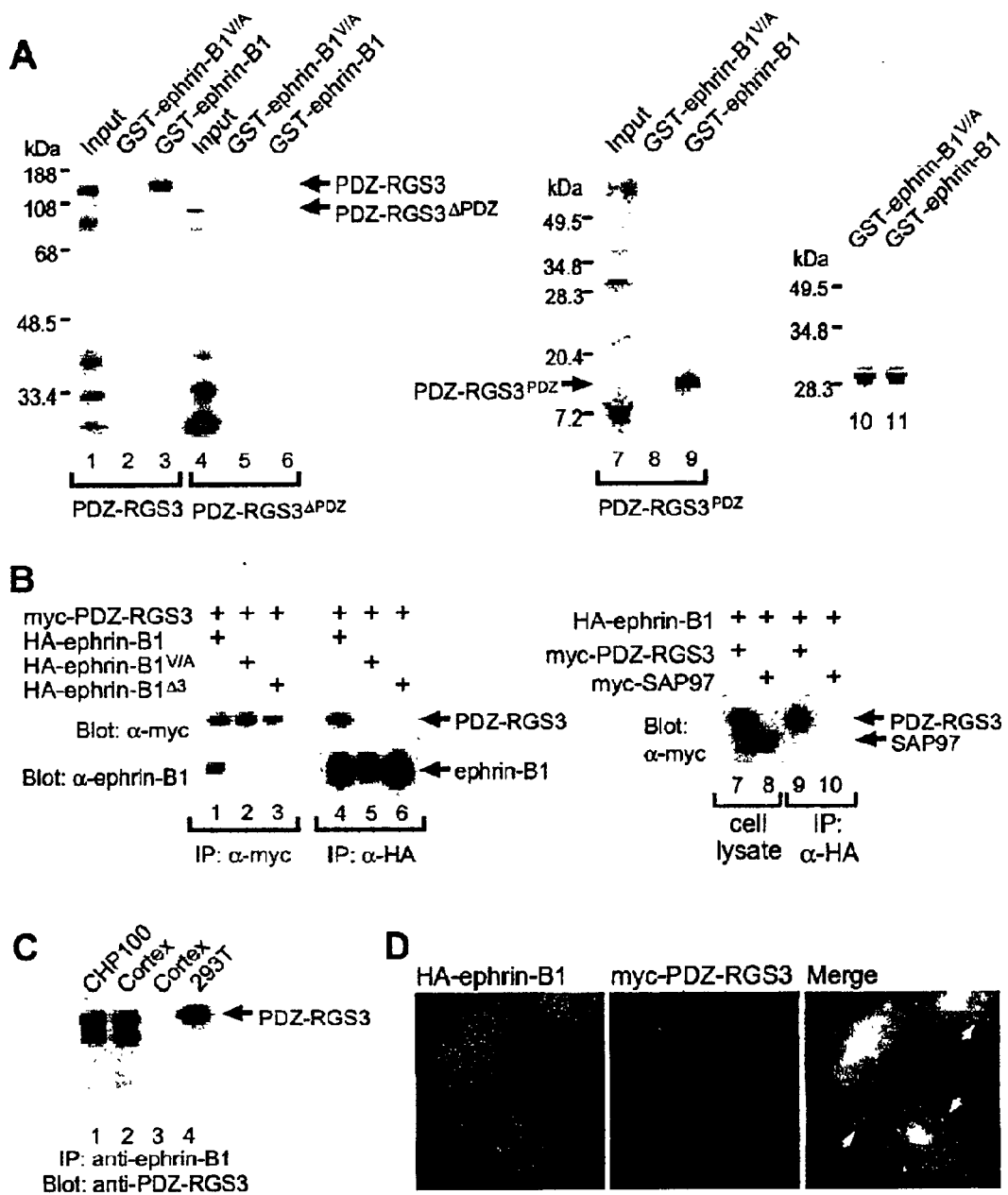
FIG. 2 shows the binding interaction between PDZ-RGS3 and B ephrin.

Fusion proteins were constructed between GST and the C-terminal 33 amino acids of ephrin-B1 (identical to the same region of ephrin-B2). In addition to the wild type sequence (GST-ephrin-B1), a version was made with the C-terrninal Valine replaced by Alanine (GST-ephrin-B1$^{V/A}$), which is expected to abolish or strongly reduce binding of PDZ proteins (Song yang et al., 1997). Affinity beads bearing GST-ephrin-B1 or GST-ephrin-B1$^{V/A}$ in similar amounts (FIG. 2A, lanes 10–11) were used to bind $^{35}$S-labelled wild type or truncated PDZ-RGS3. GST-ephrin-B1 interacted specifically with PDZ-RGS3 (FIG. 2A, lane 3), whereas GST-ephrin-B1$^{V/A}$ did not (FIG. 2A, lane 2). The PDZ domain of PDZ-RGS3 was both necessary (FIG. 2A, lanes 4–6) and sufficient (FIG. 2A, lanes 7–9) for this binding. These results indicate a direct interaction between the PDZ binding motif in the ephrin-B cytoplasmic domain, and the PDZ domain of PDZ-RGS3.

2. Binding in Transfected Cells.

Constructs encoding myc-tagged PDZ-RGS3 and HA-tagged ephrin-B1, or mutant derivatives, were co-transfected into COS cells. Lysates were then immunoprecipitated with anti-myc or anti-HA, followed by Western blot using anti-myc or a rabbit polyclonal anti-ephrin-B. Levels of wild-type and mutant proteins were comparable (FIG. 2B, lanes 4–6). Wild type ephrin-B1 and PDZ-RGS3 interacted, regardless of which was initially precipitated (FIG. 2B). This interaction was impaired by the ephrin-B1$^{V/A}$ mutation (FIG. 2B, lanes 2 and 5) and by removing the last 3 amino acids, which form most of the PDZ binding motif (ephrin-B1$^{\Delta 3}$, FIG. 2B, lanes 3 and 6). As controls, ephrin-B1 did not co-precipitate with SAP97 (FIG. 2B, lanes 7–10) or PSD95 (not shown), two PDZ proteins implicated in synapse assembly (Sheng and Pak, 2000). When fixed cells were stained for epitope-tagged PDZ-RGS3 and ephrin-B1, the two staining patterns co-localized closely (FIG. 2D). Treating the cells with a soluble EphB2-Fc fusion protein did not appear to either enhance or inhibit subsequent coprecipitation of ephrin-B1 and PDZ-RGS3 (data not shown). These results indicate constitutive binding between PDZ-RGS3 and ephrin-B1 in transfected mammalian cells.

3. Interaction in Lysates of a Neuroblastoma Cell Line, or Mouse Cortex, Where PDZ-RGS3 and Ephrin-B1 are Expressed Endogenously.

Ephrin-B1 was immunoprecipitated with a rabbit polyclonal antibody, and the subsequent Western blot was probed with an antibody to PDZ-RGS3. The results show that a PDZ-RGS3immunoreactive protein of the expected size co-precipitated with ephrin-B1 (FIG. 2C, lanes 1 and 2), indicating an interaction between PDZ-RGS3 and ephrin-B1 endogenously expressed in neural cells and tissues.

Overlapping Expression of PDZ-RGS3 and B Ephrins

Figure 3:
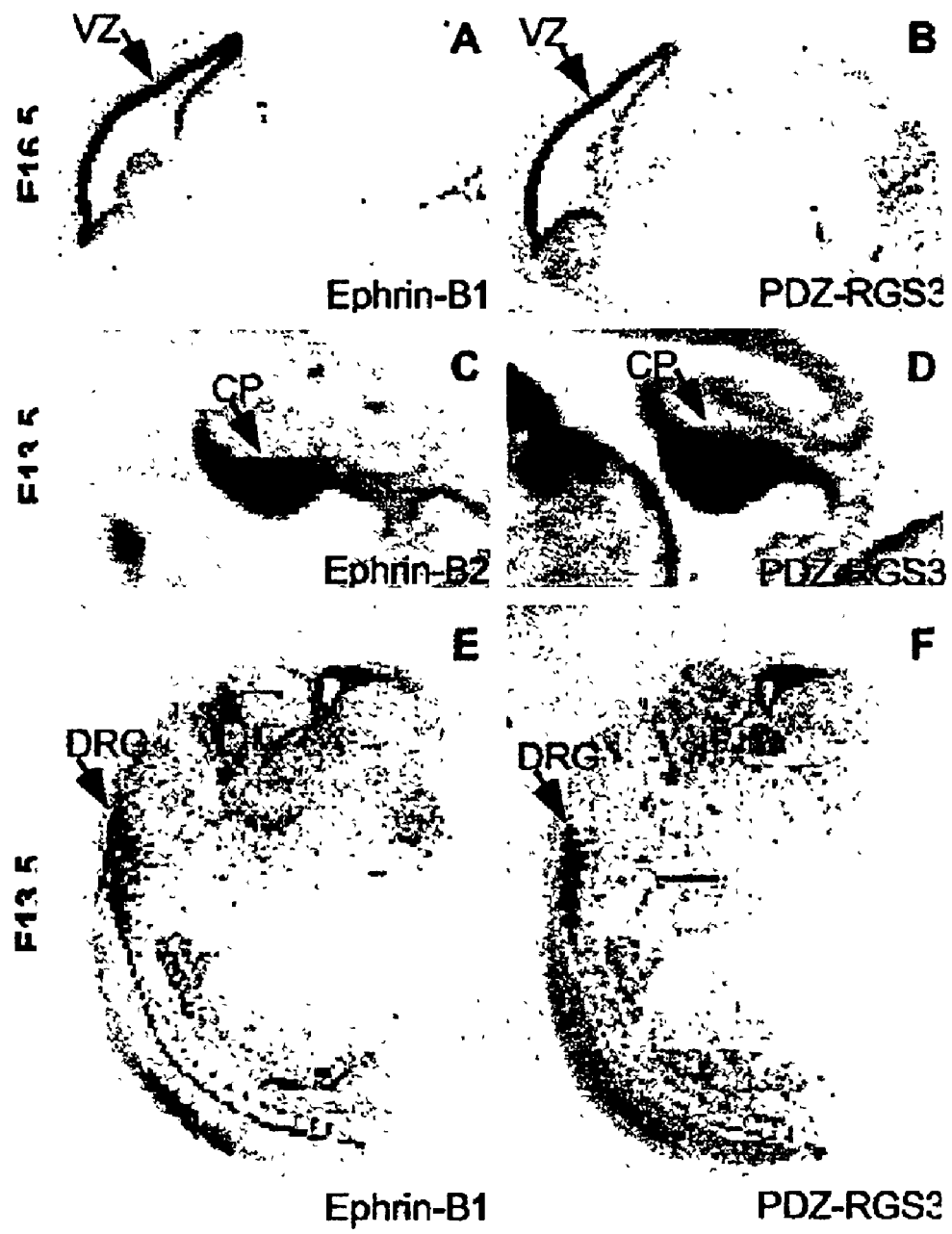
FIG. 3 shows co-localized expression of PDZ-RGS3 and B ephrins in mouse embryos. In situ hybridization was used to localize RNAs for PDZ-RGS3, ephrin-B1 or ephrin-B2, at embryonic stages indicated.

If PDZ-RGS3 and B ephrins interact functionally, it is expected they will have overlapping expression patterns. Therefore, comparison of PDZ-RGS3 expression with that of ephrin-B1 and ephrin-B2 by in situ hybridization on mouse embryos was carried out. PDZ-RGS3 co-localized with ephrin-B1 in cortical ventricular zone (FIGS. 3A and 3B), with ephrin-B2 in early cerebellar primordium (FIGS. 3C and 3D), with both ephrin-B1 and -B2 in dorsal root ganglia (FIGS. 3E and 3F) and with ephrin-B1 or -B2 in several other tissues (not shown). Taken together, the binding data described above and the closely overlapping expression patterns indicate that PDZ-RGS3 is a genuine biological interaction partner of B ephrins.

B ephrin signaling in Xeno2us embrvos mediated by PDZ-RGS3

The functional relationship between B ephrin and PDZ-RGS3 was next examined. Microinjection of ephrin-B1 RNA was previously shown to cause cell de-adhesion in *Xenopus* embryos or animal caps. The C-terminal 19 amino acids were required, whereas the extracellular domain was not (Jones, et al., 1998), showing this phenotype involves interactions of the ephrin-B1 cytoplasmic tail, and is not dependent on forward signaling. (Signaling by B ephrin lacking an extracellular domain is consistent with the constitutive signaling seen when other receptors are truncated.) This assay has the advantage that it permits multiple proteins to be expressed simultaneously and at variable levels, facilitating analysis of domain functions and interactions.

1. Requirement of the PDZ Binding Domain of Ephrin-B1 for the De-adhesion Activity.

Ephrin-B1$^{\Delta 3}$ did not cause the de-adhesion phenotype (FIG. 4) showing the PDZ binding motif is required. Next, a mutant.PDZ-RGS3 without the PDZ domain (PDZ-RGS3$^{\Delta PDZ}$) was tested. PDZ-RGS3$^{\Delta PDZ}$, alone or together with ephrin-B1, had no evident effect on the assay (FIG. 4), showing the PDZ domain of PDZ-RGS3 is also required.

2. PDZ-RGS Domain Effects on Ephrin-B1 De-adhesion Activity.

Figure 4:
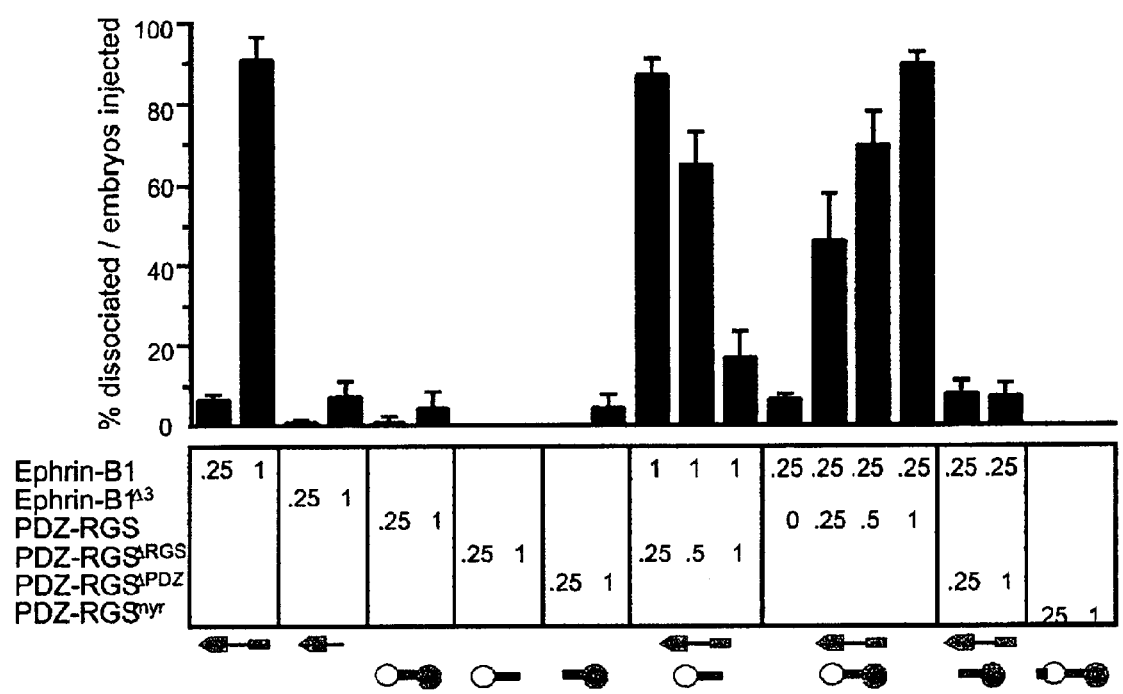
FIG. 4 shows PDZ-RGS3 mediation of cell dissociation signaling by ephrin-B1 in *Xenopus* embryos. RNAs encoding various ephrin-B1 or PDZ-RGS3 constructs were injected alone or in combinations into 2-cell embryos. Embryos were scored for dissociation at stage 8.5; error bars show SEM. RNA amounts are indicated in nanograms, and the constructs are diagrammed below: ephrin-B1 is shown in green with the C-terminal PDZ binding motif as a rectangle; PDZ-RGS3 is shown with the PDZ domain in yellow and the RGS domain in orange.

Ephrin-B1 RNAs were next co-injected with various forms of PDZ-RGS3. The first form of PDZ-RGS3 tested had the RGS domain deleted (PDZ-RGS3$^{\Delta RGS}$), to create a putative dominant negative protein. PDZ-RGS3$^{\Delta RGZ}$ alone had no effect. However, it inhibited the cell dissociation caused by ephrin-B1 in a dose dependent manner (FIG. 4). In principle, such an effect by this dominant negative protein could be to block the access of any PDZ domain-containing protein in the cell. Thus, ephrin-B1 was next co-expressed together with full length PDZ-RGS3. In this experiment, ephrin-B1 was added at a level suboptimal for dissociation, and full-length PDZ-RGS3 was found to increase idissociation in a dose-dependent manner (FIG. 4). Injection of full-length PDZ-RGS3 alone, as a control, did not cause dissociation (FIG. 4). These results indicate that PDZ-RGS3 can mediate the effect of the ephrin-B1 cytoplasmic tail, and also show the RGS domain is required.

3. Investigation of Membrane-localization of PDZ-RGS3 using PDZ-RGS3 with an Added Myristoylation Motif (PDZ-RGS3$^{myr}$).

Most, if not all, the protein from this construct localized to the membrane fraction, whereas wild-type PDZ-RGS3 expressed by itself was mainly cytosolic (data not shown). Embryos injected with PDZ-RGS3$^{myr}$ did not develop the de-adhesion phenotype (FIG. 4). This indicates that localizing PDZ-RGS3 to the membrane is not sufficient, and therefore suggests the requirement for ephrin-B1 is not simply to bring PDZ-RGS3 to the membrane. The results in the *Xenopus* assay show PDZ-RGS3 can mediate signaling induced by ephrin-B1, and that this requires both PDZ and RGS domains.

Example 2

Correlated Expression Patterns in Cerebellar Development and Possible Mechanism for Reverse Signaling Effect of Soluble EphB Receptor on Isolated Cells and its Role in Neuronal Guidance.

Identification of PDZ-RGS3, and the demonstration of a role for its RGS domain in the *Xenopus* assay suggested that one potential mechanism of reverse signaling could be to regulate signaling by a GPCR. If so, B ephrins should be expressed in the same regions as candidate GPCRs. Consequently, the expression of ephrin-B2 and EphB2 in cerebellar granule cells was of particular interest. In mice with gene disruption of SDF-1 or its receptor CXCR4, granule cells migrate prematurely from the external granule cell layer (EGL), indicating SDF-1 normally functions to prevent premature inward migration (Ma et al., 1998; Zou et al., 1998).

Figure 5:
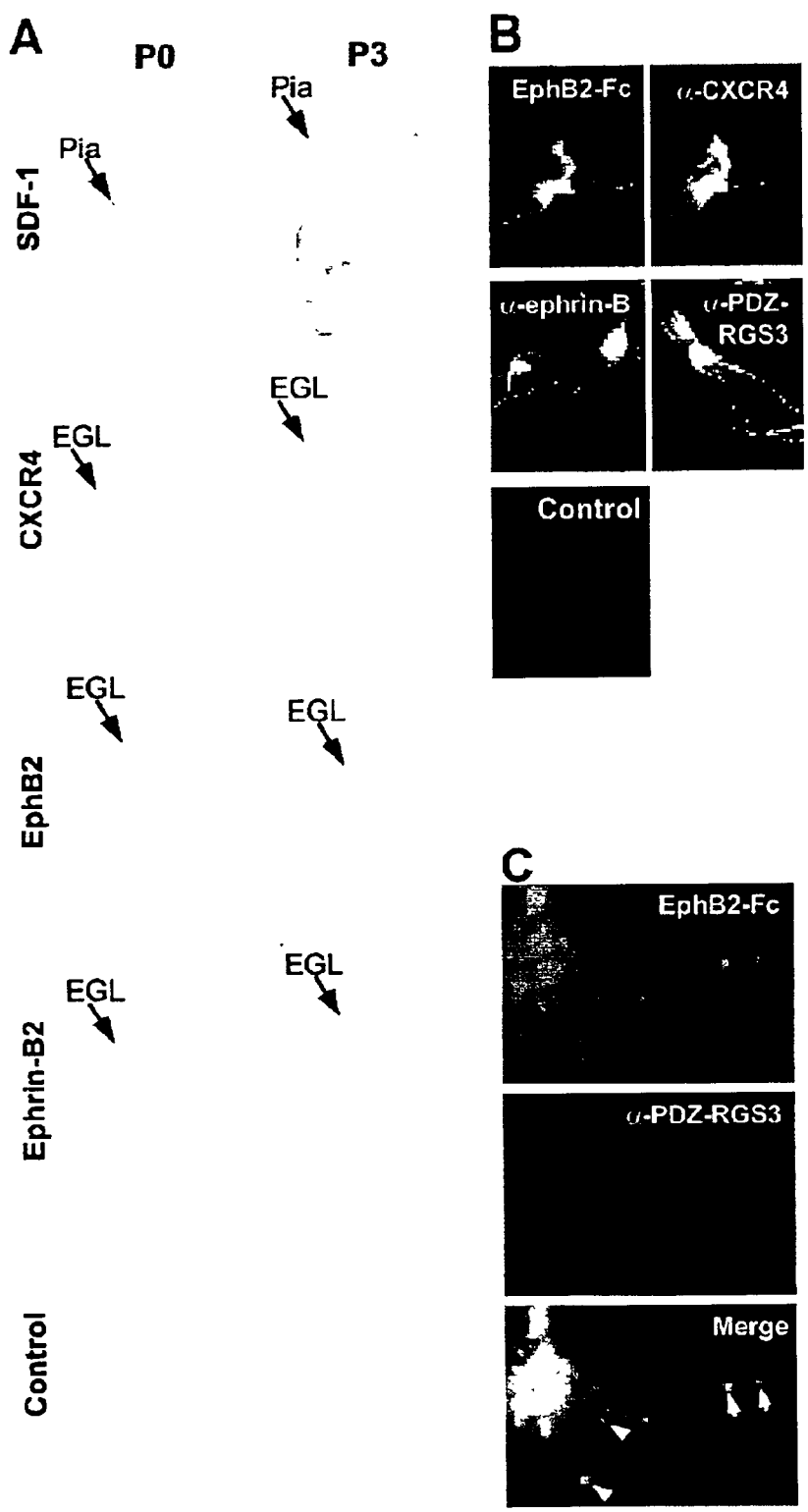
FIG. 5 shows expression in postnatal developing cerebellum.

To investigate these ideas further, expression patterns were examined by in situ hybridization. Granule cell migration normally begins around postnatal day 3 (P3) and continues into the third postnatal week (flatten, 1999). Expression of SDF-1 and CXCR4 has been reported at pre-natal stages (Zou et al., 1998; McGrath et al., 1999), and we extended this postnatally. Consistent with the prenatal pattern, we saw RNA expression for CXCR4 in the EGL, while SDF-1 was restricted more superficially to the pial membrane. Similar patterns were seen at P0 and P3 (FIG. 5A), and P6 (not shown). Ephrin-B2 was expressed in the EGL at P3, though this expression was not readily detectable at P0 (FIG. 5A). EphB2 receptor was also found in the EGL, with weak expression at P0 and strong expression at P3 (FIG. 5A).

Co-expression of B ephrin and CXCR4 was confirmed in individual purified granule cells (FIG. 5B). If PDZ-RGS3 is to mediate B ephrin reverse signaling in granule cells, these two molecules must also be expressed in the same cells. This was addressed by immunofluorescence staining, showing purified granule cells stain with antibodies to both PDZ-RGS3 and B ephrins (FIG. 5B). The species origin of these antibodies precluded co-staining, so subcellular co-localization was tested in cells that were first treated unfixed with EphB2-Fc, and subsequently permeabilized and stained with anti-PDZ-RGS3 and anti-Fc. Co-localization was seen in patches located on the cell body and cell processes (FIG. 5C). Additional staining may represent protein that is free, or associated with other binding partners, or located in intracellular compartments inaccessible to EphB2-Fc.

Regulation of Cerebellar Granule Cell Chemoattraction

To test functionally for an interaction of ephrin-B and SDF-1, a Transwell assay system was assembled using purified cerebellar granule cells. Briefly, a membrane filter with defined uniform pore size separates upper and lower chambers. Cells are placed in is the upper chamber and the number of cells that have migrated to the lower side of the filter is subsequently counted.

Figure 6:
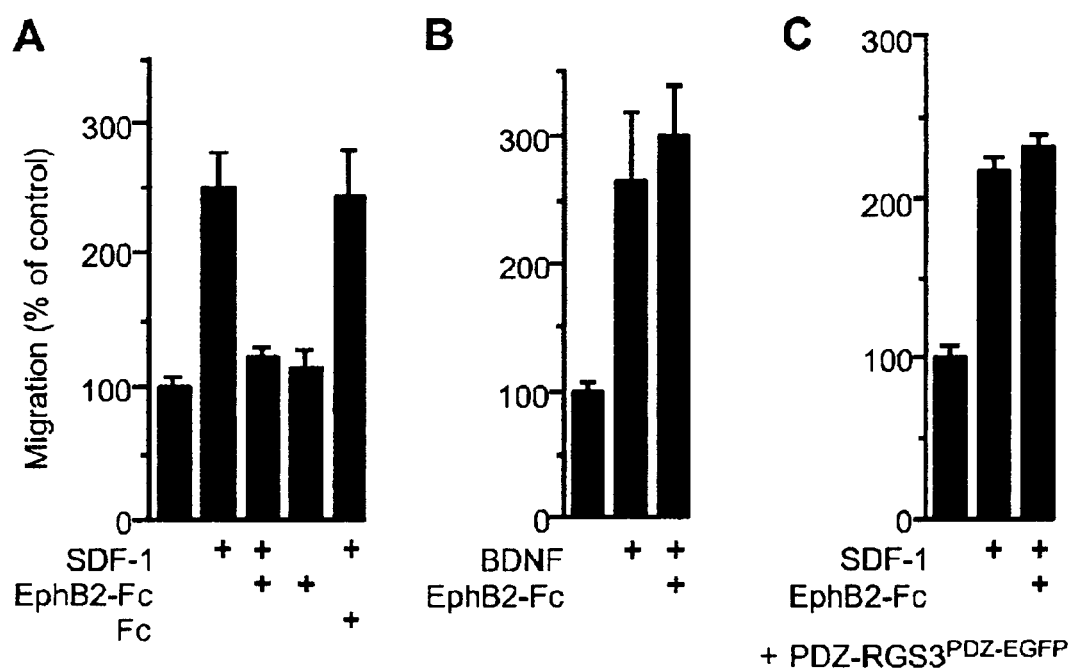
FIG. 6 shows regulation of cerebellar granule cell chemotaxis. Granule cells purified from P8 or P9 mouse cerebellum are placed in the upper chamber of a Transwell apparatus, and cells migrating to the lower side of the filter are counted. Error bars show SEM.

Initially, a chemoattractant effect of SDF-1 on cultured granule cells was investigated, something which had not been described previously. When SDF-1 was added to the lower chamber it promoted migration of granule cells ($p<0.001$, unpaired t test; FIG. 6A). Reverse signaling was triggered with soluble EphB2-Fc, which is dimerized by its Fc tag and used without further clustering (Bruckner et al., 1997). Addition of EphB2-Fc with the cells in the top chamber inhibited the chemoattractant effect of SDF-1 ($p<0.001$; FIG. 6A). Inhibition was also seen, though to a lesser degree, when EphB2 was added to the bottom chamber (not shown). Control Fc protein had no detectable effect (FIG. 6A). When EphB2-Fc was added to the top or bottom chambers in the absence of SDF-1, there was no detectable change from background levels of migration (FIG. 6A). Therefore, while this assay provided no evidence that EphB2-Fc itself acted as an attractant or repellent, it inhibited chemoattraction to SDF-1.

A potential explanation for this inhibitory effect of EphB2-Fc, not intended to be limiting in any way, could be a general effect on cell motility or responsiveness. To address this, we tested BDNF as a control attractanL BDNF was previously reported to promote cerebellar granule cell survival (Schwartz et al., 1997), and since it can act in vitro as an attractant for axons (Song et al., 1997) it was considered likely that it might also act as a chemoattractant for granule cells. Addition of BDNF to the lower chamber indeed promoted migration ($p<0.005$; FIG. 6B). Addition of EphB2-Fc to the top or bottom chamber did not inhibit cell migration towards BDNF (FIG. 6B). Thus, the inhibition by EphB2-Fc was selective for SDF-1 induced migration.

These results supported the prediction, based on analysis of PDZ-RGS3, that reverse signaling might affect a heterotrimeric G protein signaling pathway. To assess this further, a dominant negative form of PDZ-RGS3 was tested. To overcome a major obstacle for such an experiment, namely, the difficulty of expressing genes with high enough efficiency in primary neurons, a Sindbis viral vector was used, based on reports of efficient gene transfer into a wide variety of cells. Enhanced green fluorescent protein (Chalfie et al., 1994) was incorporated into the constructs, so infected cells could be traced. The dominant negative construct in these experiments was the PDZ domain of PDZ-RGS3, fused to EGFP (PDZ-RGS3$^{3PDZ-EGFP}$). As in uninfected cells, when granule cells were infected with control EGFP virus, SDF-1 acted as a chemoattractant, and thus was inhibited by EphB2-Fc (data not shown). When PDZ-RGS3$^{PDZ-EGFP}$ was introduced into the cells, SDF-1 still acted as a chemoattractant ($p<0.001$; FIG. 6C). However, the inhibitory effect of EphB2-Fc on this chemoattraction was now blocked (FIG. 6C).

Example 3

Effect of PDZ-RGS3 on Leukocyte Migration

Effect of Soluble EphB Recettor on Isolated Cells and its Role in Leukocvte Migration.

As stated above, identification of PDZ-RGS3, and the demonstration of a role for its RGS domain in the *Xenopus* assay suggested that one potential mechanism of reverse signaling was to regulate signaling by a GPCR (G protein-coupled receptor). Recently, Wu et al., Nature, 410, 948 (2001), showed that the secreted protein Slit, previously known for its role of repulsion in axon guidance and neuronal migration, also inhibited leukocyte chemotaxis induced by chemotactic factors, i.e. chemokines.

Regulation of Cerebellar Granule Cell Chemoattraction

To investigate this concept with PDZ-RGS3 protein, a transwell system is assembled wherein the effect of leukocyte migration, in the presence of an appropriate chemokine such as SDF-1 with or without PDZ-RGS3 protein, is monitored.

To test functionally for an interaction of the GPCR ephrin B and SDF-1, a transwell assay system can be assembled using purified leukocytes. As described above, a membrane filter with defined uniform pore size separates upper and lower chambers. Cells are placed in the upper chamber and the number of cells that have migrated to the lower side of the filter is subsequently counted.

Initially, the chemoattractant effect of an appropriate chemokine, such as SDF-1, on cultured leukocyte cells is investigated. The chemokine is added to the lower chamber to promote migration of leukocyte cells. Reverse signaling is then triggered with soluble EphB2-Fc, which is dimerized by its Fc tag and used without further clustering as above. EphB2-Fc is then added with the cells in the top chamber to look for inhibition of the chemoattractant effect of the chemokine, in this case, SDF-1. Control Fc protein is also added to the top chamber, and expected to have no effect.

BDNF can also be added to the chambers as a control attractant, to investigate any general effect on cell motility of responsiveness exhibited by EphB2-Fc, and to determine whether the effect on migration of leukocytes by the assayed chemokine, in this case SDF-1, is selective. If addition of EphB2-Fc to the top or bottom chamber does not inhibit cell migration towards BDNF, then inhibition by EphB2-Fc will be selective for the chemokine (SDF-1) induced migration observed.

Example 4

Another Possible Function of PDZ-RGS3

A second potential function for transmembrane ligands is to allow bi-directional signaling. Again, the ephrins have provided a particularly good model system to investigate this idea. Reverse signaling through B ephrins has been demonstrated biochemically by ligand phosphorylation. Evidence of important developmental roles has come from genetic and embryological studies of whole embryos or tissues. Herein, characterization of cell biological effects, and molecular mechanisms of ephrin-B reverse signaling, have been detailed. In addition, the experiments have led to other conclusions, uncovering a novel pathway for extracellular control of heterotrimeric G proteins, and demonstrating selective regulation of responsiveness to guidance factors as a mechanism that can regulate neuronal migration.

Molecular and Cellular Mechanisms of Reverse Signaling

Reverse signaling at a molecular level was investigated by screening for proteins that bind the B ephrin cytoplasmic domain, leading to identification of PDZ-RGS3 in a yeast two-hybrid assay. Ile two proteins also bind one another in an in vitro GST pull-down assay, and by co-immunoprecipitation from lysates of transfected cells, or neural cells and tissues that express the two proteins endogenously. In situ hybridization shows a close overlap of expression patterns for PDZ-RGS3 with one or other of the three known B ephrins in several parts of the nervous system. Taken together these results indicate that PDZ-RGS3 is a genuine biological interaction partner of B ephrins.

The domain structure of PDZ-RGS3 suggests how this protein might function, but the following is in no means intended to be limiting of function. PDZ domains are known to bind to a short conserved motif at the C-terminus of many membrane proteins (Songyang et al., 1997; Sheng and Pak, 2000). A sequence fitting this motif is found at the C-terminus of all known B ephrins, and the experiments herein indicate that the PDZ domain of PDZ-RGS3 binds the ephrin-B C-terminus. Tyrosine residues are found in the binding motif (YYKV-carboxy terminus) suggesting potential control of binding by phosphorylation, and the PDZ-GRS3/ephrin B interaction did not appear to be regulated by EphB receptor binding. The presence of an RGS domain suggested PDZ-RGS3 might interact with downstream effector pathways. In fact, a Xenopus embryo cell dissociation assay showed that PDZ-RGS3 mediates effects of the B ephrin cytoplasmic tail, in a manner dependent on both its PDZ and RGS domains. While the Xenopus assay was well suited to test the function and interaction of individual domains, such a system does not readily assess the effect of Eph receptor binding, the downstream pathways, and the relevance to guidance. Due to the involvement of the RGS domain in signaling, as well as the cerebellar expression of ephrins, cerebellar granule cells were tested for an effect of reverse signaling on the action of SDF-1, which acts through a GPCR. As expected, soluble EphB2-Fc selectively regulated the guidance response to SDF-1, and this regulation was blocked by a truncated version of PDZ-RGS3 lacking the RGS domain. A molecular model based on such studies, in no way intended to be the only possible model, is shown in FIG. 7A.

Figure 7:
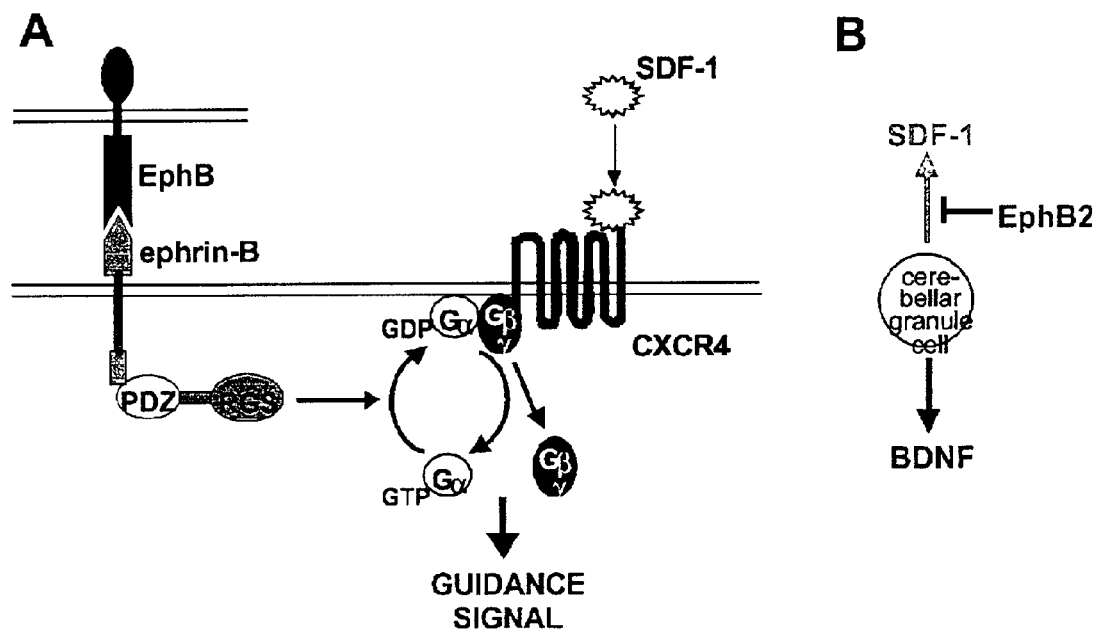
FIG. 7 shows molecular and cellular mechanisms of reverse signaling.

At the level of cell biological effects, the above examples show that reverse signaling induced by Eph receptor can regulate cellular guidance (FIG. 7B). Specifically, soluble EphB2-Fc selectively inhibited SDF-1 chemoattraction of cultured cerebellar granule neurons. Although reverse signaling through B ephrins has been investigated more extensively, soluble EphA receptors can affect adhesion in cell lines (Huai and Drescher, ; Davy et al., 1999), and it will be interesting to see if this may reflect similar developmental functions or signaling pathways. The above data on the regulation of cerebellar granule cell guidance by EphB2-Fc, SDF-1, and BDNF suggests a model, in no way intended to be the only model, for control of cell migration in cerebellar development, as described further below. It is envisioned, in fact, that the above observations also fit with other developmental functions proposed for B ephrin reverse signaling, in blood vessel formation, rhombomere compartmentation, and axon pathway selection, all involving regulation of migration or morphogenesis.

Regarding the mechanism for signal transduction across the cell membrane, as with other PDZ proteins that bind B ephrins (Torres et al., 1998; Bruckner et al., 1999; Lin et al., 1999), the association with PDZ-RGS3 was seen constitutively, and did not appear to be modulated by treating cells with soluble EphB2-Fc. This suggests regulated association between B ephrin and PDZ-RGS3 is not a likely mechanism of signal transduction. An alternative could be regulation of clustering or subcellular localization. It is known that EphB2-Fc can cluster B ephrins and associated PDZ proteins into membrane rafts (Bruckner et al., 1999). 1eterotrimeric G proteins have also been localized to rafts (Simons and Ikonen, 1997). Therefore, one model could be that Eph receptor binding could cluster B ephrins into rafts, or other subcellular structures, and this could bring associated PDZ-RGS3 into proximity with the appropriate G proteins, resulting in inhibition of their activity. It is finally worth noting that not only the PDZ binding motif, but at least 33 amino acids of the B ephrin cytoplasmic tail are strongly conserved, and it is likely that additional protein interactions play a role in signaling, either through independent pathways or in collaboration with PDZ-RGS3.

Heterotrimeric G protein signaling

Heterotrimeric G proteins are classically controlled by receptors in the seven—transmembrane family. RGS proteins were identified as GAPs for G proteins, and contain additional protein modules, including PDZ domains, which could potentially allow control of G proteins by other signaling pathways. Moreover, PDZ and RGS domains can associate through protein-protein interactions, as in the case of GIPC/NIP/SEMCAP-1, a PDZ protein that binds the RGS protein GAIP, and also interacts with cell surface semaphorins and neuropilins (De Vries et al., 1998; Cai and Reed, 1999; Wang et al., 1999). The observation thal B ephrin signaling can be mediated by PDZ-RGS3, in a manner requiring both PDZ and RGS domains, provides a possible explanation, in no way intended to be limiting, for the presence of both PDZ and RGS domains in this protein. The regulation of a G protein pathway by ephrin reverse signaling also provides a potentially general mechanism that can allow heterotrimeric G protein pathways to be regulated through cell surface receptors, other than classical seven-transmembrane GPCRs.

It is not clear to what degree PDZ-RGS3 interactions might be general or specific. Most known RGS proteins, including human RGS3, are GAPs for the $G\alpha i$ or $G\alpha q$ subfamily of G proteins. Our results are therefore very consistent with studies showing CXCR4 is coupled to $G\alpha i2$ (Moepps et al., 1997). On the other hand, experiments on purified proteins or transfected cells suggest the specificity of RGS proteins for individual G proteins, and likewise the specificity of PDZ proteins for individual binding motifs, may not be high. Differences in affinity or kinetics could provide some degree of specificity. Alternatively, biological specificity may come from expression patterns, since these intracellular interactions would require the proteins to be expressed in the same cell. In keeping with this idea, we find a close correlation in the expression patterns of PDZ-RGS3 and B ephrins, suggesting there may be a special biological relationship between these proteins. Finally, a further layer of specificity could be provided by subcellular localization. The observation that PDZ-RGS3 failed to signal when targeted to the membrane by myristoylation could be consistent with a model where B ephrins not only bring PDZ-RGS3 to the membrane, but also target it to signaling complexes containing the appropriate G proteins.

Cerebellar Granule Cell Migration

The inward migration of cerebellar granule cells from the EGL is one of the best characterized models of neuronal migration. The genetic demonstration that SDF-1 and its receptor CXCR4 are required for normal granule cell migration provided the first evidence of chemokines as regulators of neural development. Specifically, the phenotype of premature granule cell migration, taken together with the embryonic expression of SDF-1 in the pia mater overlying the cerebellum, suggested a model wherein SDF-1 prevents premature inward migration of cerebellar granule cells by chemoattraction toward the pia (Ma et al., 1998; Zou et al., 1998; McGrath et al., 1999). The presently claimed invention supports this model, by experimental results showing SDF-1 expression in the pia at postnatal stages that span the onset of granule cell migration, and by demonstrating that SDF-1 is a chemoattractant for cultured cerebellar granule cells.

Experiments further show that reverse signaling induced by soluble EphB2-Fc can inhibit the effect of SDF-1 on cerebellar granule cells. This provides the first functional evidence for an effect of ephrin signaling on cerebellar granule cells. A developmental role for the interaction of these signaling pathways is supported by the correlated expression of ephrinB2, SDF-1, and their receptors during cerebellar development.

The following model is based on the above functional assays of primary cultured cerebellar granule cells, the expression patterns of the relevant molecules during cerebellar development, and the phenotypes of SDF-1 and CXCR4 gene disrupted mice. During the period when some granule cells remain in the EGL, and others have migrated inwards, expression of SDF-1 and CXCR4 persists. To reconcile the inconsistency that SDF-1 prevents inward migration by chemoattracting granule cells toward the pia, and yet some cells still break away to migrate inward, it is proposed that when granule cells are ready to migrate, they may lose responsiveness to SDF-1.

Such a change in responsiveness could be mediated at least in part by B ephrins and EphB receptors, a model consistent with the observed inhibitory effect of EphB2-Fc on SDF-1 responsiveness of granule cells, as well as the up-regulation of ephrin-B2 and is EphB2 gene expression by granule cells around the time of migration onset in mouse cerebellum. Ephrin-B1 and EphB2 were also reported to be expressed by migrating granule cells in chick cerebellum (Karam et al., 2000). Consistent with this model, explant culture experiments show that at the time of migration onset, cerebellar granule cells lose their responsiveness to a chemoattractant in the pia. When granule cells start to travel inwards, they presumably still need to be responsive to other signals, allowing them to migrate and find their destination in the internal granule cell layer. BDNF could promote this inward migration, since it is a chemoattractant for cerebellar granule cells, as shown here, and since the inward migration is impaired by BDNF gene knockout. The selectivity observed for EphB2 in inhibiting responsiveness to SDF-1 but not BDNF suggests a developmental model where ephrin signaling could act as a switch, changing the balance of preference from SDF-1 to other guidance cues. Such a model, while consistent with the presently known data, is in no way intended to limit other possible models that may also be consistent.

Finally, it is interesting to consider why regulation in this context might be mediated by ephrins, providing a bi-directional signaling system requiring direct cell-cell contact. One possibility could be autocrine signaling by granule cells. An alternative model is suggested by the observation that developing granule cells do not migrate independently, but rather in contact with other granule cells and radial glial fibers (Rakic, 1990; Hatten, 1999). Persistence of SDF-1 expression may ensure that granule cells do not migrate in isolation. Cell-cell contact could then activate ephrin signaling, and allow migration once granule cells are assembled with the correct cellular partners. Other models are also possible.

Contact-mediated cell-cell signaling can allow spatial precision, and bi-directional control. Forward signaling through Eph receptors is well established to precisely guide cell and axon migration. Genetic and embryological studies have shown B ephrin reverse signaling can affect processes involving migration or morphogenesis, and the presently claimed inventions shows that soluble EphB-Fc receptor can directly regulate cell guidance. Ephrin signaling can thus allow contact-mediated bi-directional regulation of guidance. This may allow coordinated movement within a cell population, or mutual regulation of interacting cell populations.

Our results also provide a mechanism for a receptor not in the seven-transmembrane class to regulate G protein signaling. In addition to the effect seen herein on cerebellar cells, it is proposed that ephrin reverse signaling affects leukocyte chemotaxis to chemokines, thereby providing a means for treatment of inflammation and other diseases. More generally, it is proposed that regulation through PDZ-RGS proteins provides a pathway to control many processes regulated by a proteins.

The presently claimed invention provides a means for selective regulation of responsiveness to guidance factors. Throughout the nervous system, the immune system, and elsewhere, such mechanisms are likely to have critical roles in allowing migrating cells and axons to appropriately modulate their responses, as they leave their point of origin, pass intermediate guideposts, and arrive at their final targets.

References

Adams, R. H. Wilkinson, G. A. Weiss. C., Diella. F., Gale, N. W.,Deutsch, U., Risau, W., and Klein, R. (1999). Roles of ephrinB ligands and EphB receptors in cardiovascular development: demarcation of arterial/venous domains, vascular morphogenesis, and sprouting angiogenesis. Genes Dev. 13, 295–306.

Arshavsky, V. Y., and Pugh, E. N. J. (1998). Lifetime regulation of G protein-effector complex; emerging importance of RGS proteins. Neuron 20, 11–14.

Bargmann, C. I., and Kaplan, J. M. (1998). Signal transduction in the Caenorhabditis elegans nervous system. Annu. Rev. Neurosci. 21, 279–308.

Bennett, B. D., Zeigler, F. C., Gu, Q., Fendly, B., Goddard, A. D., Gillett, N., and Matthews, W. (1995). Molecular cloning of a ligand for the EPH-related receptor protein-tyrosine kinase Htk. Proc. Natl. Acad. Sci. USA 92, 1866–1870.

Bergemann, A. D., Cheng, H.-J., Brambilla, R., Klein, R., and Flanagan, J. G. (1995). ELF2, a new member of the Eph ligand family, is segmentally expressed in mouse embryos in the region of the hindbrain and newly forming somites. Mol. Cell. Biol. 15, 4921–4929.

Bergemann, A. D., Zhang, L., Chiang, M.-K., Brambilla, R., Klein, R., and Flanagan, J. G. (1998). Ephrin-B3, a ligand for the receptor EphB3, expressed at the midline of the developing neural tube. Oncogene 16, 471–480.

Bruckner, K., Labrador, J. P., Scheiffele. P., Herb, A., Seeburg, P. H., and Klein, R. (1999). EphrinB ligands recruit GRIP family PDZ adaptor proteins into raft membrane microdomains. Neuron 22, 511–524.

Bruckner, K., Pasquale, E. B., and Klein, R. (1997). Tyrosine phosphorylation of transmembrane ligands for Eph receptors. Science 275, 1640–1643.

Cai, H. B., and Reed, R. R. (1999). Cloning and characterization of neuropilin-1-interacting protein: A PSD-95/Dlg/ZO-1 domain-containing protein that interacts with the cytoplasmic domain of neuropilin-1. J. Neurosci. 19, 6519–6527.

Chalfie, M., Tu, Y., Euskirchen, G., Ward, W. W., and Prasher, D. C. (1994). Green fluorescent protein as a marker for gene expression. Science 263, 802–805.

Ciossek, T., Lerch, M. M., and Ulrich, A. (1995). Cloning, characterization, and differential expresssion of MDK2 and MDK5, two novel receptor tyrosine kinases of the eck/eph family. Oncogene 11, 2085–2095.

Corset, V., Nguyen-ba-Charvet, K. T., Forcet, C., Moyse, E., Chedotal, A., and Mehlen, P. (2000). Netrin-1-mediated axon outgrowth and cAMP production requires interaction with adenosine A2b receptor. Nature 407, 747–750.

Craven, S. E., and Bredt, D. S. (1998). PDZ proteins organize synaptic signaling pathways. Cell 93,495–498.

Davis, S., Gale, N. W., Aldrich, T. H., Maisonpierre, P. C., Lhotak, V. Pawson, T., Goldfarb. M., and Yancopoulos, G. D. (1994). Ligands for EPH-related receptor tyrosine kinases that require membrane attachment or clustering for activity. Science 266, 816–819.

Davy, A., Gale, N. W., Murray, E. W., Klinghoffer, R. A., Soriano, P., Feuerstein, C., and Robbins, S. M. (1999). Compartmentalized signaling by GPI-anchored ephrin-A5 requires the Fyn tyrosine kinase to regulate cellular adhesion. Genes Dev. 13, 3125–3135.

De Vries, L., and Farquhar, M. G. (1999). RGS proteins: more than just GAPS for heterotrimeric G proteins. Trends in Cell Biology 9, 138–144.

De Vries, L., Lou, X. J., Zhao, G., Zheng, B., and Farquhar, M. G. (1998). GIPC, a PDZ domain containing protein, interacts specifically with the C terminus of RGS-GAIP. Proc. Natl. Acad. Sci. USA 95, 12340–12345.

Drescher, U., Bonhoeffer, F., and Muller, B. (1997). The Eph family in retinal axon guidance. Curr. Op. Neurobiol. 7, 75–80.

Druey, K. M., Blumer, K. J., Kang, V. H., and Kehrl, J. H. (1996). Inhibition of G-proteinmediated MAP kinase activation by a new mammalian gene family. Nature 379, 742–746.

Flanagan, J. G., Chan, D. C., and Leder, P. (1991). Transmembrane form of the kit ligand growth factor is determined by alternative splicing and is missing in the SI$^d$ mutant. Cell 64,1025–1035.

Flanagan, J. G., and Vanderhaeghen, P. (1998). The ephrins and Eph receptors in neural development. Annu. Rev. Neurosci. 21, 309–345.

Frisen, J., Holmberg, J., and Barbacid, M. (1999). Ephrins and their Eph receptors: multitalented directors of embryonic development. EMBO J. 18, 5159–5165.

Garner, C. C., Nash, J., and Huganir, R. L. (2000). PDZ domains in synapse assembly and signaling. Trends Cell Biol. 10, 274–280.

Gerety, S. S., Wang, H. U., Chen, Z. F., and Anderson, D. J. (1999). Symmetrical mutant phenotypes of the receptor EphB4 and its specific transmembrane ligand ephrin-B2 in cardiovascular development. Mol. Cell 4, 403–414.

Hajdu-Cronin, Y. M., Chen, W. J., Patikoglou, G., Koelle, M. R., and Sternberg, P. W. (1999). Antagonism between G(o)alpha and G(q)alpha in Caenorhabditis elegans: the RGS protein EAT-16 is necessary for G(o)alpha signaling and regulates G(q)alpha activity. Genes Dev. 13, 1780–1793.

Hart, M. J., Jiang, X., Kozasa, T., Roscoe, W., Singer, W. D., Gilman, A. G., Sternweis, P. C., and Bollag, G. (1998). Direct stimulation of the guanine nucleotide exchange activity of p115 RhoGEF by Galphal3. Science 280, 2112–2114.

Hatten, M. E. (1985). Neuronal regulation of astroglial morphology and proliferation in vitro, J. Cell Biol. 100, 384–396.

Hatten, M. E. (1999). Central nervous system neuronal migration. Annu. Rev. Neurosci. 22,511–539.

Henkemeyer, M., Orioli, D., Henderson, J. T., Saxton, T. M., Roder, J., Pawson, T., and Klein, R. (1996). Nuk controls pathfinding of commissural axons in the mammalian central nervous system. Cell 86, 35–46.

Holder, N., and Klein, R. (1999). Eph receptors and ephrins: effectors of morphogenesis. Development 126, 2033–2044.

Holland, S. J., Gale, N. W., Mbalamu, G., Yancopoulos, G. D., Henkemeyer, M., and Pawson, T. (1996). Bidirectional signalling through the EPH-family receptor Nuk and its transmembrane ligand. Nature 383, 722–725.

Hollenberg, S. M., Stemglanz, R., Cheng, P. F., and Weintraub, H. (1995). Identification of a new family of tissue-specific basic helix-loop-helix proteins with a two-hybrid system. Mol. Cell Biol. 15, 3813–3822.

Huai, J., and Drescher, U. An ephrin-A-dependent signaling pathway controls integrin function and is linked to the tyrosine phosphorylation of a 120 kDa protein. J. Biol. Chem. e-publication ahead of print, Jones, T. L., Chong, L. D., Kim, J., Xu, R. H., Kung, H. F., and Daar, I. O. (1998). Loss of cell adhesion in *Xenopus laevis* embryos mediated by the cytoplasmic domain of Xlerk, an erythropoietin-producing hepatocellular ligand. Proc. Natl. Acad. Sci. USA 95, 576581.

Karam, S. D., Burrows, R. C., Logan, C., Koblar, S., Pasquale, E. B., and Bothwell, M. (2000). Eph receptors and ephrins in the developing chick cerebellum: relationship to sagittal patterning and granule cell migration. J. Neurosci. 20, 6488–6500.

Kehrl, J. H. (1998). Heterotrimeric G protein signaling—roles in immune function and finetuning by RGS proteins. Immunity 8, 1–10.

Kozasa, T., Jiang, X., Hart, M. J., Sternweis, P. M., Singer, W. D., Gilman, A. G., Bollag, G., and Sternweis, P. C. (1998). p115 RhoGEF, a GTPase activiating protein for Galpha12 and Galpha13. Science 280, 2109–2111.

Lin, D., Gish, G. D., Son-yang, Z., and Pawson, T. (1999). The carboxyl terminus of B class ephrins constitutes a PDZ domain binding motif. J. Biol. Chem. 274, 3726–3733.

Ma, Q., Jones. D., Borghesani, P. R., Segal, R. A., Nagasawa. T., Kishimoto, T., Bronson, R. T., and Springer, T. A. (1998). Impaired B-lymphopoiesis, myelopoiesis, and derailed cerebellar neuron migration in CXCR4- and SDF-1-deficient mice. Proc. Natl. Acad. Sci. USA 95, 9448–9453.

Massague, J., and Pandiella, A. (1993). Membrane-anchored Growth factors. Annu. Rev. Biochem. 62, 515–541.

McGrath, K. E., Koniski, A. D., Maltby, K. M., McGann, J. K., and Palis, J. (1999). Embryonic expression and function of the chemokine SDF-1 and its receptor, CXCR4. Dev. Biol. 213, 442–456.

Melkhers, F., Rolink, A. G., and Schaniel, C. (1999). The role of chemokines in regulating cell migration during humoral immune responses. Cell 99, 351–354.

Mellitzer, G., Xu, Q., and Wilkinson, D. G. (1999). Eph receptors and ephrins restrict cell intermingling and communication. Nature 400, 77–81.

Moepps, B., Frodl, R., Rodewald, H. R., Baggiolini, M., and Gierschik, P. (1997). Two murine homologues of the human chemokine receptor CXCR4 mediating stromal cell-derived factor lalpha activation of Gig are differentially expressed in vivo. Eur. J. Immunol. 27, 2102–2112.

Nakamura, F., Kalb, R. G., and Strittmatter, S. M. (2000). Molecular basis of semaphorinmediated axon guidance. J. Neurobiol. 44, 219–229.

Parent, C. A., and Devreotes, P. N. (1999). A cell's sense of direction. Science 284, 765–770.

Pfeffer, S., and Ullrich, A. (1985). Epidermal growth factor. Is the precursor a receptor? Nature 313, 184.

Rakic, P. (1990). Principles of neural cell migration. Experientia 46, 882–891.

Rupp, R. A., Snider, L., and Weintraub, H. (1994). *Xenopus* embryos regulate the nuclear localization of XMyoD. Genes Dev. 8, 1311–1323.

Schwartz, P. M., Borghesani, P. R., Levy, R. L., Pomeroy, S. L., and Segal, R. A. (1997). Abnormal cerebellar development and foliation in BDNF-/-mice reveals a role for neurotrophins in CNS patterning. Neuron 19, 269–281.

Sheng, M., and Pak, D. T. (2000). Ligand-gated ion channel interactions with cytoskeletal and signaling proteins. Annu. Rev. Physiol. 62, 755–778.

Simons, K., and Ikonen, E. (1997). Functional rafts in cell membranes. Nature 387, 569-572.

Song, H. J., Ming, G. L., and Poo, M. M. (1997). cAMP-induced switching in turning direction of nerve growth cones. Nature 388, 275–279.

Son-yang, Z., Fanning, A. S., Fu, C., Xu, J., Marfatia, S. M., Chishti, A. H., Crompton, A., Chan, A. C., Anderson, J. M., and Cantley, L. C. (1997). Recognition of unique carboxylterminal motifs by distinct PDZ domains. Science 275, 73–77.

Suzuki, G., Sawa, H., Kobayashi, Y., Nakata, Y., Nakagawa, K., Uzawa, A., Sakiyarna, H., Kakinuma, S., Iwabachi, K., and Nagashima, K. (1999). Pertussis toxin-sensitive signal controls the trafficking of thymocytes across the corticomedullary junction in the thymus. J. Immunol. 162, 5981–5985.

Torres, R., Firestein, B. L., Dong, H. L., Staudinger, J., Olson, E. N., Huganir, R. L., Bredt, D. S., Gale, N. W., and Yancopoulos, G. D. (1998). PDZ proteins bind, cluster, and synaptically colocalize with Eph receptors and their ephrin ligands. Neuron 21, 1453–1463.

Vancura, K. L., and Jay, D. G. (1998). G proteins and axon growth. Sem. Neurosci. 9, 209219.

Wang, H. U., Chen, Z. F., and Anderson, D. J. (1998). Molecular distinction and angiogenic interaction between embryonic arteries and veins revealed by ephrin-B2 and its receptor EphB4. Cell 93, 741–753.

Wang, L. H., Kalb, R. G., and Strittmnatter, S. M. (1999). A PDZ protein regulates the distribution of the transmembrane semaphorin, M-SemF. J. Biol. Chem. 274, 14137–14146.

Watson, S., and Arkinstall, S. (1994). The G-protein linked receptor factsbook. (London: Academic Press).

Xu, Q., Mellitzer, G., Robinson, V., and Wilkinson, D. G. (1999). In vivo cell sorting in complementary segmental domains mediated by Eph receptors and ephrins. Nature 399, 267–271.

Zheng, B., De Vries, L., and Farquhar, M. G. (1999). Divergence of RGS proteins: evidence for the existence of six mammalian RGS subfamilies. Trends Biochem. Sci. 24, 411–414.

Zou, Y. R., Kottmann, A. H., Kuroda, M., Taniuchi, I., and Littman, D. R. (1998). Function of the chemokine receptor CXCR4 in haematopoiesis and in cerebellar development. Nature 393, 595–599.

---

What is claimed is:

1. An isolated protein comprising an amino acid sequence as set forth in SEQ ID NO: 1.

2. An isolated protein according to claim 1, wherein the protein mediates cell signaling in the presence of ephrin-B1.

3. A pharmaceutical composition comprising an effective dose of an isolated protein comprising: the amino acid sequence as set forth in SEO.ID.NO.1; a suitable carrier; and optionally, additional active or inert ingredients such as diluents, stabilizers, and excipients.

* * * * *

SEQUENCE LISTING

```
<160> NUMBER OF SEQ ID NOS: 6

<210> SEQ ID NO 1
<211> LENGTH: 930
<212> TYPE: PRT
<213> ORGANISM: Mus musculus

<400> SEQUENCE: 1

Met Asn Arg Phe Asn Gly Leu Cys Lys Val Cys Ser Glu Arg Arg Tyr
1               5                   10                  15

Arg Gln Ile Thr Ile Arg Arg Gly Lys Asp Gly Phe Gly Phe Thr Ile
            20                  25                  30

Cys Cys Asp Ser Pro Val Arg Val Gln Ala Val Asp Ser Gly Gly Pro
        35                  40                  45

Ala Glu Arg Ala Gly Leu Gln Gln Leu Asp Thr Val Leu Gln Leu Asn
    50                  55                  60

Glu Arg Pro Val Glu His Trp Lys Cys Val Glu Leu Ala His Glu Ile
65                  70                  75                  80

Arg Ser Cys Pro Ser Glu Ile Ile Leu Leu Val Trp Arg Val Val Pro
                85                  90                  95
```

```
Gln Ile Lys Pro Gly Pro Asp Gly Gly Val Leu Arg Arg Ala Ser Cys
            100                 105                 110

Lys Ser Thr His Asp Leu Leu Ser Pro Pro Asn Lys Arg Glu Lys Asn
            115                 120                 125

Cys Thr His Gly Ala Pro Val Arg Pro Glu Gln Arg His Ser Cys His
            130                 135                 140

Leu Val Cys Asp Ser Ser Asp Gly Leu Leu Gly Gly Trp Glu Arg
145                 150                 155                 160

Tyr Thr Glu Val Gly Lys Arg Ser Gly Gln His Thr Leu Pro Ala Leu
                165                 170                 175

Ser Arg Thr Thr Thr Pro Thr Asp Pro Asn Tyr Ile Ile Leu Ala Pro
            180                 185                 190

Leu Asn Pro Gly Ser Gln Leu Leu Arg Pro Val Tyr Gln Glu Asp Thr
            195                 200                 205

Ile Pro Glu Glu Pro Gly Thr Thr Lys Gly Lys Ser Tyr Thr Gly
210                 215                 220

Leu Gly Lys Lys Ser Arg Leu Met Lys Thr Val Gln Thr Met Lys Gly
225                 230                 235                 240

His Ser Asn Tyr Gln Asp Cys Ser Ala Leu Arg Pro His Ile Pro His
                245                 250                 255

Ser Ser Tyr Gly Thr Tyr Val Thr Leu Ala Pro Lys Val Leu Val Phe
            260                 265                 270

Pro Val Phe Val Gln Pro Leu Asp Leu Cys Asn Pro Ala Arg Thr Leu
            275                 280                 285

Leu Leu Ser Glu Glu Leu Leu Leu Tyr Glu Gly Arg Asn Lys Thr Ser
            290                 295                 300

Gln Val Thr Leu Phe Ala Tyr Ser Asp Leu Leu Leu Phe Thr Lys Glu
305                 310                 315                 320

Glu Glu Pro Gly Arg Cys Asp Val Leu Arg Asn Pro Leu Tyr Leu Gln
                325                 330                 335

Ser Val Lys Leu Gln Glu Gly Ser Ser Glu Asp Leu Lys Phe Cys Val
            340                 345                 350

Leu Tyr Leu Ala Glu Lys Ala Glu Cys Leu Phe Thr Leu Glu Ala His
            355                 360                 365

Ser Gln Glu Gln Lys Arg Val Cys Trp Cys Leu Ser Glu Asn Ile
            370                 375                 380

Ala Lys Gln Gln Gln Leu Ala Ala Pro Pro Thr Glu Arg Lys Met Phe
385                 390                 395                 400

Glu Thr Glu Ala Asp Glu Lys Glu Met Pro Leu Val Glu Gly Lys Gly
                405                 410                 415

Pro Gly Ala Glu Glu Pro Ala Pro Ser Lys Asn Pro Ser Pro Gly Gln
            420                 425                 430

Glu Leu Pro Pro Gly Gln Asp Leu Pro Pro Ser Lys Asp Pro Ser Pro
            435                 440                 445

Ser Gln Glu Leu Pro Ala Gly Gln Asp Leu Pro Pro Arg Lys Asp Ser
            450                 455                 460

Pro Gly Gln Glu Ala Ala Pro Gly Pro Glu Ser Pro Ser Ser Glu Asp
465                 470                 475                 480

Ile Ala Thr Cys Pro Lys Pro Gln Ser Pro Glu Thr Ser Thr Ser
                485                 490                 495

Lys Asp Ser Pro Pro Gly Gln Gly Ser Ser Pro Thr Thr Glu Leu Pro
            500                 505                 510

Ser Cys Gln Gly Leu Pro Ala Gly Gln Glu Ser Thr Ser Gln Asp Pro
```

```
                515                 520                 525
Leu Leu Ser Gln Glu Pro Pro Val Ile Pro Glu Ser Ser Ala Ser Val
        530                 535                 540
Gln Lys Arg Leu Pro Ser Gln Glu Ser Pro Ser Ser Leu Gly Ser Leu
545                 550                 555                 560
Pro Glu Lys Asp Leu Ala Glu Gln Thr Ile Ser Ser Gly Glu Pro Pro
                565                 570                 575
Val Ala Thr Gly Ala Val Leu Pro Ala Ser Arg Pro Asn Phe Val Ile
            580                 585                 590
Pro Glu Val Arg Leu Asp Asn Ala Tyr Ser Gln Leu Asp Gly Ala His
        595                 600                 605
Gly Gly Ser Ser Gly Glu Asp Glu Ala Glu Glu Gly Glu Gly
    610                 615                 620
Gly Glu Gly Glu Glu Asp Glu Glu Asp Asp Thr Ser Asp Asp Asn Tyr
625                 630                 635                 640
Gly Asp Arg Ser Glu Ala Lys Arg Ser Ser Leu Ile Glu Thr Gly Gln
                645                 650                 655
Gly Ala Glu Gly Gly Phe Ser Leu Arg Val Gln Asn Ser Leu Arg Arg
            660                 665                 670
Arg Thr His Ser Glu Gly Ser Leu Leu Gln Glu Ser Arg Gly Pro Cys
        675                 680                 685
Phe Ala Ser Asp Thr Thr Leu His Cys Ser Asp Gly Glu Gly Ala Thr
    690                 695                 700
Ser Thr Trp Ala Ile Pro Ser Pro Arg Thr Leu Lys Lys Glu Leu Gly
705                 710                 715                 720
Arg Asn Gly Gly Ser Met His His Leu Ser Leu Phe Phe Thr Gly His
                725                 730                 735
Arg Lys Met Ser Gly Thr Asp Leu Thr Glu Cys Asp Glu Ala Ser Arg
            740                 745                 750
Lys Arg Lys Ser Lys Asn Ile Ala Lys Asp Met Lys Asn Lys Leu Ala
        755                 760                 765
Ile Phe Arg Arg Arg Asn Glu Ser Pro Gly Ala Gln Pro Ala Ser Lys
    770                 775                 780
Thr Asp Lys Thr Thr Lys Ser Phe Lys Pro Thr Ser Glu Glu Ala Leu
785                 790                 795                 800
Lys Trp Ser Glu Ser Leu Glu Lys Leu Leu Leu His Lys Tyr Gly Leu
                805                 810                 815
Glu Val Phe Gln Ala Phe Leu Arg Thr Glu Phe Ser Glu Glu Asn Leu
            820                 825                 830
Glu Phe Trp Leu Ala Cys Glu Asp Phe Lys Lys Val Lys Ser Gln Ser
        835                 840                 845
Lys Met Ala Ala Lys Ala Lys Lys Ile Phe Ala Glu Phe Ile Ala Ile
    850                 855                 860
Gln Ala Cys Lys Glu Val Asn Leu Asp Ser Tyr Thr Arg Glu His Thr
865                 870                 875                 880
Lys Glu Asn Leu Gln Ser Ile Thr Arg Gly Cys Phe Asp Leu Ala Gln
                885                 890                 895
Lys Arg Ile Phe Gly Leu Met Glu Lys Asp Ser Tyr Pro Arg Phe Leu
            900                 905                 910
Arg Ser Asp Leu Tyr Leu Asp Leu Ile Asn Gln Lys Lys Met Ser Pro
        915                 920                 925
Pro Leu
    930
```

<210> SEQ ID NO 2
<211> LENGTH: 519
<212> TYPE: PRT
<213> ORGANISM: Homo sapiens

<400> SEQUENCE: 2

```
Met Phe Glu Thr Glu Ala Asp Glu Lys Arg Glu Met Ala Leu Glu Glu
 1               5                  10                  15

Gly Lys Gly Pro Gly Ala Glu Asp Ser Pro Ser Lys Glu Pro Ser
            20                  25                  30

Pro Gly Gln Glu Leu Pro Pro Gly Gln Asp Leu Pro Asn Lys Asp
        35                  40                  45

Ser Pro Ser Gly Gln Glu Pro Ala Pro Ser Gln Glu Pro Leu Ser Ser
 50                  55                  60

Lys Asp Ser Ala Thr Ser Glu Gly Ser Pro Gly Pro Asp Ala Pro
 65                  70                  75                  80

Pro Ser Lys Asp Val Pro Pro Cys Gln Glu Pro Pro Ala Gln Asp
            85                  90                  95

Leu Ser Pro Cys Gln Asp Leu Pro Ala Gly Gln Glu Pro Leu Pro His
            100                 105                 110

Gln Asp Pro Leu Leu Thr Lys Asp Leu Pro Ala Ile Gln Glu Ser Pro
        115                 120                 125

Thr Arg Asp Leu Pro Pro Cys Gln Asp Leu Pro Pro Ser Gln Val Ser
 130                 135                 140

Leu Pro Ala Lys Ala Leu Thr Glu Asp Thr Met Ser Ser Gly Asp Leu
145                 150                 155                 160

Leu Ala Ala Thr Gly Asp Pro Pro Ala Ala Pro Arg Pro Ala Phe Val
                165                 170                 175

Ile Pro Glu Val Arg Leu Asp Ser Thr Tyr Ser Gln Lys Ala Gly Ala
            180                 185                 190

Glu Gln Gly Cys Ser Gly Asp Glu Glu Asp Ala Glu Glu Ala Glu Glu
        195                 200                 205

Val Glu Gly Glu Glu Gly Glu Glu Asp Glu Asp Glu Asp Thr Ser
210                 215                 220

Asp Asp Asn Tyr Gly Glu Arg Ser Glu Ala Lys Arg Ser Ser Met Ile
225                 230                 235                 240

Glu Thr Gly Gln Gly Ala Glu Gly Gly Leu Ser Leu Arg Val Gln Asn
                245                 250                 255

Ser Leu Arg Arg Arg Thr His Ser Glu Gly Ser Leu Leu Gln Glu Pro
            260                 265                 270

Arg Gly Pro Cys Phe Ala Ser Asp Thr Thr Leu His Cys Ser Asp Gly
        275                 280                 285

Glu Gly Ala Ala Ser Thr Trp Gly Met Pro Ser Pro Ser Thr Leu Lys
290                 295                 300

Lys Glu Leu Gly Arg Asn Gly Gly Ser Met His His Leu Ser Leu Phe
305                 310                 315                 320

Phe Thr Gly His Arg Lys Met Ser Gly Ala Asp Thr Val Gly Asp Asp
                325                 330                 335

Asp Glu Ala Ser Arg Lys Arg Lys Ser Lys Asn Leu Ala Lys Asp Met
            340                 345                 350

Lys Asn Lys Leu Gly Ile Phe Arg Arg Arg Asn Glu Ser Pro Gly Ala
        355                 360                 365

Pro Pro Ala Gly Lys Ala Asp Lys Met Met Lys Ser Phe Lys Pro Thr
```

```
                370             375             380
Ser Glu Glu Ala Leu Lys Trp Gly Glu Ser Leu Glu Lys Leu Leu Val
385                 390                 395                 400

His Lys Tyr Gly Leu Ala Val Phe Gln Ala Phe Leu Arg Thr Glu Phe
                405                 410                 415

Ser Glu Glu Asn Leu Glu Phe Trp Leu Ala Cys Glu Asp Phe Lys Lys
                420                 425                 430

Val Lys Ser Gln Ser Lys Met Ala Ser Lys Ala Lys Lys Ile Phe Ala
                435                 440                 445

Glu Tyr Ile Ala Ile Gln Ala Cys Lys Glu Val Asn Leu Asp Ser Tyr
450                 455                 460

Thr Arg Glu His Thr Lys Asp Asn Leu Gln Ser Val Thr Arg Gly Cys
465                 470                 475                 480

Phe Asp Leu Ala Gln Lys Arg Ile Phe Gly Leu Met Glu Lys Asp Ser
                485                 490                 495

Tyr Pro Arg Phe Leu Arg Ser Asp Leu Tyr Leu Asp Leu Ile Asn Gln
                500                 505                 510

Lys Lys Met Ser Pro Pro Leu
                515

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gtgggcaagc gcagtggcca gcacaccctg                                    30

<210> SEQ ID NO 4
<211> LENGTH: 30
<212> TYPE: DNA
<213> ORGANISM: Artificial Sequence
<220> FEATURE:
<223> OTHER INFORMATION: PRIMER

<400> SEQUENCE: 4
ccgcacatcc cgcattccag ttacggcacc                                    30

<210> SEQ ID NO 5
<211> LENGTH: 16
<212> TYPE: PRT
<213> ORGANISM: Artificial Sequence
<220> FEATURE:
<223> OTHER INFORMATION: ANTIBODY ANTIGEN

<400> SEQUENCE: 5

Thr Ile Pro Glu Glu Pro Gly Thr Thr Thr Lys Gly Lys Ser Tyr Thr
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: ANTIBODY ANTIGEN

<400> SEQUENCE: 6

Arg Ser Asp Leu Tyr Leu Ile Asn Gln Lys Lys Met Ser Pro Pro Leu
1               5                   10                  15
```